(12) United States Patent
Iwanaga

(10) Patent No.: US 6,494,577 B2
(45) Date of Patent: Dec. 17, 2002

(54) OPHTHALMOLOGIC APPARATUS

(75) Inventor: Tomoyuki Iwanaga, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 127 days.

(21) Appl. No.: 09/808,178

(22) Filed: Mar. 15, 2001

(65) Prior Publication Data

US 2001/0028440 A1 Oct. 11, 2001

(30) Foreign Application Priority Data

Mar. 17, 2000 (JP) ........................................ 2000-076135
Mar. 27, 2000 (JP) ........................................ 2000-085634
May 30, 2000 (JP) ........................................ 2000-160304

(51) Int. Cl.⁷ ............................................... A61B 3/14
(52) U.S. Cl. ..................................................... 351/208
(58) Field of Search .............................. 351/204, 205, 351/206, 208, 209, 211, 221, 214

(56) References Cited

U.S. PATENT DOCUMENTS 5,467,151 A    11/1995  Kohayakawa .............. 351/213
5,889,577 A  *  3/1999  Kohayakawa .............. 351/211
5,894,337 A     4/1999  Okinishi et al. ........... 351/205
5,988,815 A  * 11/1999  Maus et al. ................ 351/221
6,022,108 A  *  2/2000  Yoshida et al. ............ 351/208
6,192,269 B1   2/2001  Okumura et al. .......... 600/479

* cited by examiner

Primary Examiner—George Manuel
(74) Attorney, Agent, or Firm—Fitzpatrick, Cella, Harper & Scinto

(57) ABSTRACT

An ophthalmologic apparatus has a measuring system for measuring inherent information of an eye, a detecting system for detecting a standard position of the eye, an actuator for actuating an optical system including the measuring system and the detecting system, and a controller. In the controller, a processing procedure of alignment between the standard position of the eye and the measuring system is divided with respect to each of a plurality of areas, and a control method for at least one of the measuring system and the actuator is changed in accordance with an area in which the standard position is located.

24 Claims, 16 Drawing Sheets

"ALIGNMENT COMPLETE"

OPHTHALMOLOGIC APPARATUS

BACKGROUND OF THE INVENTION

1. Field of the Invention

The present invention relates to an ophthalmologic apparatus for obtaining information inherent in an eye of a patient, such as information relating to eye refractive power, eye fundus image, and volume of eye fundus blood flow.

2. Related Background Art

In this type of an ophthalmologic apparatus, before an examination, it is necessary to perform positioning (alignment) of an examination unit to an eye of a person to be examined (patient). This alignment is performed as follows. An operator observes an anterior eye part image of a patient displayed on a display unit, and operates an operation device to rough align an examination unit with an eye. After a cornea reflected image or a pupil image due to an index light flux projected to an cornea of the eye is displayed on the display unit, the operator operates the operation device such that the cornea reflected image or the pupil image is aligned with a mark for alignment displayed around an optical axis, whereby exact alignment is performed. In this ophthalmologic apparatus, an acceptable range with respect to alignment between a standard position of the eye and an optical axis of the examination unit is related to an acceptable degree of deviation in a measurement value due to change in a position of the examination unit, whereby an alignment acceptable range, that is, a measurement acceptable area is determined.

Recently, a method for performing automatic alignment of the examination unit to be actuated by an actuator has been proposed. In this method, a reflected index image from the eye is detected photoelectrically, and the actuator is controlled so as to align an optical axis of the examination unit with the detected reflected index image. Here, there are a method for controlling the actuator continuously after the standard position of the eye enters the measurement acceptable area, a method for stopping control of the actuator when the standard position of the eye enters the measurement acceptable area and restarting control of the actuator when the standard position of the eye is apart from the measurement acceptable area, and the like. However, in the former method, even if the apparatus is in the state where a measurement value is obtained with a high precision, the actuator may be repeatedly controlled more than necessary. This prevents rapid measurement. On the other hand, in the latter method, when the standard position of the eye is located in an end of the measurement acceptable area and thus control of the actuator is stopped, the standard position of the eye may be apart from the measurement acceptable area in accordance with slight movement of the eye. This prevents stable measurement.

Here, although a degree is different depending on personal equation or disease factor, it is known that a vertex of the cornea is eccentric to the center of the pupil in most of the human eyes. Thus, when exact alignment of the apparatus and the eye is performed to the center of the index image, the pupil is eccentric to a light ring, whereby a light flux necessary for measurement may be shaded by the pupil. This prevents stable measurement.

Commonly, a radius of the pupil in the eye of the human becomes larger or smaller by accommodation of eye function. Thus, it is required that an operator is in practice with respect to alignment between the pupil and the apparatus examination unit. Also, in the apparatus for automatic alignment, since complicated processing is necessary to detect the center of the pupil photoelectrically, it takes a long time, whereby preventing the rapidity of measurement.

SUMMARY OF THE INVENTION

The present invention is started from the above attention. One object of the present invention is to provide an ophthalmologic apparatus in which stable measurement can be performed rapidly. Another object of the present invention is to provide an ophthalmologic apparatus in which simplification and miniaturization can be attained.

To attain the above object, according to one aspect of the present invention, there is provided an ophthalmologic apparatus comprising:

a measuring system for measuring inherent information of an eye;

a detecting system for detecting a standard position of the eye;

an actuator for actuating an optical system including the measuring system and the detecting system; and a controller for dividing a processing procedure of alignment between the standard position of the eye and the measuring system in accordance with each of a plurality of areas, and changing a control method for at least one of the measuring system and the actuator in accordance with an area in which the standard position is located.

In the aspect of the invention, there may be provided an ophthalmologic apparatus, further comprising an light source for measurement and index projection commonly, and an optical system for performing both pickup of an index image and observation of the eye.

In the aspect of the invention, there may be provided an ophthalmologic apparatus, wherein the controller controls to perform measurement by the measuring system plural times.

In the aspect of the invention, there may be provided an ophthalmologic apparatus, wherein the plurality of areas have a first area which is a measurement acceptable area of a relative position between the standard position and the measuring system, a second area which is within the first area and is smaller than the first area, and a third area which is outside the first and second areas, and the controller has a first step of determining that the standard position is within which of the first, second and third areas, a second step of controlling the actuator so as to enter the standard position into the second area, and a third step of allowing measurement, and performs the second and third steps when the standard position is within the first area in the first step, performs the third step when the standard position is within the second area in the first step, and performs the second step when the standard position is within the third area in the first step.

In the aspect of the invention, there may be provided an ophthalmologic apparatus, wherein the detecting system has a system for projecting an index light flux for alignment and dividing the index light flux reflected from the eye into a plurality of light flux.

In the aspect of the invention, there may be provided an ophthalmologic apparatus, further comprising a display for displaying the eye with the plurality of areas.

In the aspect of the invention, there is provided an ophthalmologic apparatus, wherein the controller controls to start measurement automatically when the standard position of the eye is within the processing procedure.

According to other aspect of the present invention, there is provided an ophthalmologic apparatus comprising:

a measuring system for measuring inherent information of an eye;

an index system for projecting an index light flux onto a cornea of the eye;

an image pickup device for picking an anterior eye part of the eye together with an index image of an index light flux reflected from the cornea;

a display for displaying an anterior eye part image picked by the image pickup device together with the index image;

an operation device for allowing an operator to operate; and a controller for detecting a position of the index image in accordance with operation by the operation device, and performing control to display an alignment mark representing a position of the index image around the index image on the display.

In the aspect of the invention, there may be provided an ophthalmologic apparatus, further comprising an indicator for indicating to the operator whether the index image is within an area represented by the alignment mark or not.

In the other aspect of the invention, there may be provided an ophthalmologic apparatus, wherein the controller determines whether the index image is within an area represented by the alignment mark or not, and controls to automatically repeat measurement executed by the measuring system predetermined times when the index image is within the area.

In the other aspect of the invention, there may be provided an ophthalmologic apparatus, wherein the controller determines whether the index image is within an area represented by the alignment mark or not, and controls to automatically stop measurement executed by the measuring system when the index image is not within the area.

In the other aspect of the invention, there may be provided an ophthalmologic apparatus, wherein after the measurement is stopped, the controller determines whether the index image is within the area represented by the alignment mark or not, and controls to automatically restart the measurement when the index image is within the area.

According to other aspect of the present invention, there is provided an ophthalmologic apparatus comprising:

a measuring system for measuring inherent information of an eye;

an index system for projecting an index light flux onto a cornea of the eye;

a first detecting system for detecting a position of a pupil of the eye;

a second detecting system for detecting a position of an index image in accordance with a reflected light flux from the cornea by a light flux projected from the index system;

an actuator for actuating a unit including the measuring system, the index system, the first detecting system and the second detecting system; and a controller for performing a first step of controlling the actuator so as to align an optical axis of the measuring system with the position of the center of the pupil detected by the first detecting system, a second step of determining an area of a predetermined range including the position of the index image as a center detected by the second detecting system, approximately simultaneous with completion of the first step, and a third step of controlling the actuator so as to enter the index image into the area.

In the other aspect of the invention, there may be provided an ophthalmologic apparatus further comprising an image pickup device for picking an anterior eye part of the eye and a display for displaying the anterior eye part image, wherein the area determined in the second step is displayed on the display.

In the other aspect of the invention, there is provided an ophthalmologic apparatus further comprising a light source commonly used for the index system and the measuring system.

In the other aspect of the invention, there may be provided an ophthalmologic apparatus further comprising an image pickup device commonly used for the first and second detecting systems.

In the other aspect of the invention, there may be provided an ophthalmologic apparatus, wherein the controller controls so as to project the index light flux into the eye by the index system after the first step is performed.

In the other aspect of the invention, there may be provided an ophthalmologic apparatus, wherein the second detecting system includes an aperture having a plurality of holes in a plane approximately vertical to the optical axis.

According to other aspect of the present invention there is provided an ophthalmologic apparatus comprising:

a measuring system for measuring inherent information of an eye;

an index system for projecting an index light flux onto a cornea of the eye;

a first detecting system for detecting a position of a pupil of the eye;

a second detecting system for detecting a position of an index image in accordance with a reflected light flux from the cornea by a light flux projected from the index system;

an actuator for actuating a unit including the measuring system, the index system, the first detecting system and the second detecting system; and a controller for performing a first step of controlling the actuator so as to align an optical axis of the measuring system with the position of the center of the pupil detected by the first detecting system, a second step of, approximately simultaneous with completion of the first step, obtaining a position of a vertex of the cornea from the position of the index image detected by the second detecting system and determining an area of a predetermined range including the position of the vertex of the cornea as a center, and a third step of controlling the actuator so as to enter the vertex of the cornea into the area.

In the other aspect of the invention, there may be provided an ophthalmologic apparatus further comprising an image pickup device for picking an anterior eye part image of the eye and a display for displaying the anterior eye part image, wherein the area determined in the second step is displayed on the display.

In the other aspect of the invention, there may be provided an ophthalmologic apparatus further comprising a light source commonly used for the index system and the measuring system.

In the other aspect of the invention, there may be provided an ophthalmologic apparatus further comprising an image pickup device commonly used for the first and second detecting systems.

In the other aspect of the invention, there may be provided an ophthalmologic apparatus, wherein the controller controls so as to project the index light flux into the eye by the index system after the first step is performed.

In the other aspect of the invention, there may be provided an ophthalmologic apparatus, wherein the second detecting system includes an aperture having a plurality of holes in a plane approximately vertical to the optical axis.

Further objects of the present invention and embodiments thereof are clear in explanation of the embodiments below.

DESCRIPTION OF THE PREFERRED EMBODIMENTS

First Embodiment

Figure 1:
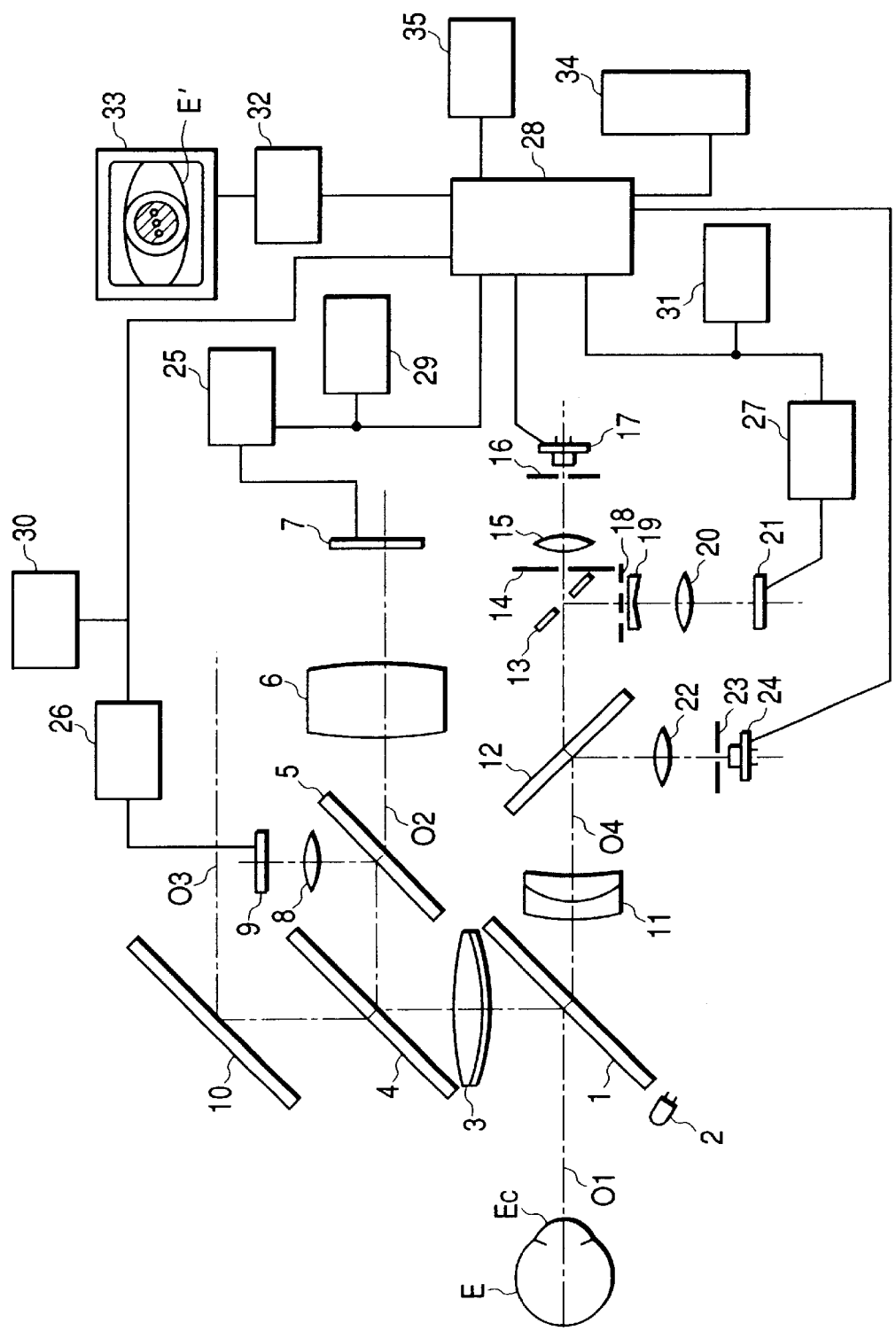
FIG. 1 shows an optical structure according to a first embodiment.

FIG. 1 shows an optical structure of an ophthalmologic examination apparatus according to a first embodiment of the present invention. On an optical path 01 in front of an eye E of a patient (subject to be examined), a dichroic mirror 1 is disposed opposite to the eye E. An illuminating light source 2 such as a light emitting diode for emitting near-infrared light to illuminate the anterior eye part of the eye E, is disposed between the eye E and the dichroic mirror 1 outside an optical axis. An objective lens 3 and a dichroic mirror 4 are disposed in the reflecting direction of the dichroic mirror 1. A dichroic mirror 5, an imaging lens 6 and an image pickup device 7 such as a CCD camera are disposed on an optical path 02 in the reflecting direction of the dichroic mirror 4. The image pickup device 7 is disposed in a position approximately conjugate with the vicinity of the anterior eye part. An observing optical system for the anterior eye part is constructed by the objective lens 3, the dichroic mirrors 4 and 5, the imaging lens 6 and the image pickup device 7.

An imaging lens 8 and an image pickup device 9 are disposed in the reflecting direction of the dichroic mirror 5. An optical system for index image pickup is constructed by the objective lens 3, the dichroic mirrors 4 and 5, the imaging lens 8 and the image pickup device 9. The image pickup device 9 is a CCD camera or the like, and is arranged in a position approximately conjugate with the vicinity of the anterior eye part. A mirror 10 is disposed in the transmitting direction of the dichroic mirror 4. A projecting optical system (not shown) for fixing the eye E is disposed on an optical path 03 in the reflecting direction of the mirror 10.

On the other hand, an objective lens 11, a beam splitter 12 such as a half mirror, a partial hole mirror 13, an aperture (stop) 14, a projection lens 15, an index plate 16 and a measurement light source 17 are disposed on an optical path 04 in the transmitting direction of the dichroic mirror 1. The measurement light source 17 is a light source for emitting near-infrared light having a wavelength of several tens of nm longer than that of the illuminating light source 2. A projecting optical system for measurement light is constructed by the objective lens 11, the beam splitter 12, the partial hole mirror 13, the aperture 14, the projection lens 15, the index plate 16 and the measurement light source 17.

A six holes aperture (stop) 18 having six holes outside an optical axis, a six divided prism 19, a relay lens 20 and an image pickup device 21 such as a CCD camera are disposed in the reflecting direction of the partial hole mirror 13. A receiving optical system for eye refractive power measurement is constructed by the objective lens 11, the beam splitter 12, the partial hole mirror 13, the six holes aperture 18, the six divided prism 19, the relay lens 20 and the image pickup device 21.

Also, a projection lens 22, an index plate 23 and an index light source 24 such as a light emitting diode for emitting near-infrared light are disposed in the reflecting direction of the beam splitter 12. A projecting optical system for a cornea index is constructed by the objective lens 11, the beam splitter 12, the projection lens 22, the index plate 23 and the index light source 24.

The dichroic mirror 1 has a characteristic such that most of light of wavelength emitted from the measurement light source 17 and the index light source 24 are transmitted to reflect a portion of the light and such that light of wavelength emitted from the illuminating light source 2 is reflected. Also, the dichroic mirror 4 has a characteristic such that visible light is transmitted and near-infrared light is reflected. Further, the dichroic mirror 5 has a characteristic such that light of wavelength emitted from the measurement light source 17 and the index light source 24 are reflected and such that light of wavelength emitted from the illuminating light source 2 is transmitted.

Outputs of the image pickup devices 7, 9 and 21 are connected with a computer 28 through A/D converters 25, 26 and 27, and connected with image memories 29, 30, 31, respectively. The measurement light source 17, the index light source 24, the image memories 29, 30, 31, a display unit 33 through a D/A converter, an actuator 34 such as a driving motor and an operation device 35 in which various switches are arranged are connected with the computer 28. The switches in the operation device 35 include a switch for operating the actuator 35, a switch for starting measurement and a switch for setting the number of measurements.

An examination unit is constructed by a plurality of optical systems mentioned above. The examination unit is mounted on a base movable in three axis directions, and electrically actuated by the actuator 34 in a Z-axis direction of an optical axis, and bidirections of, an X-axis direction and a Y-direction orthogonal to each other, which are orthogonal to the Z-axis direction.

Figures 2, 2A:
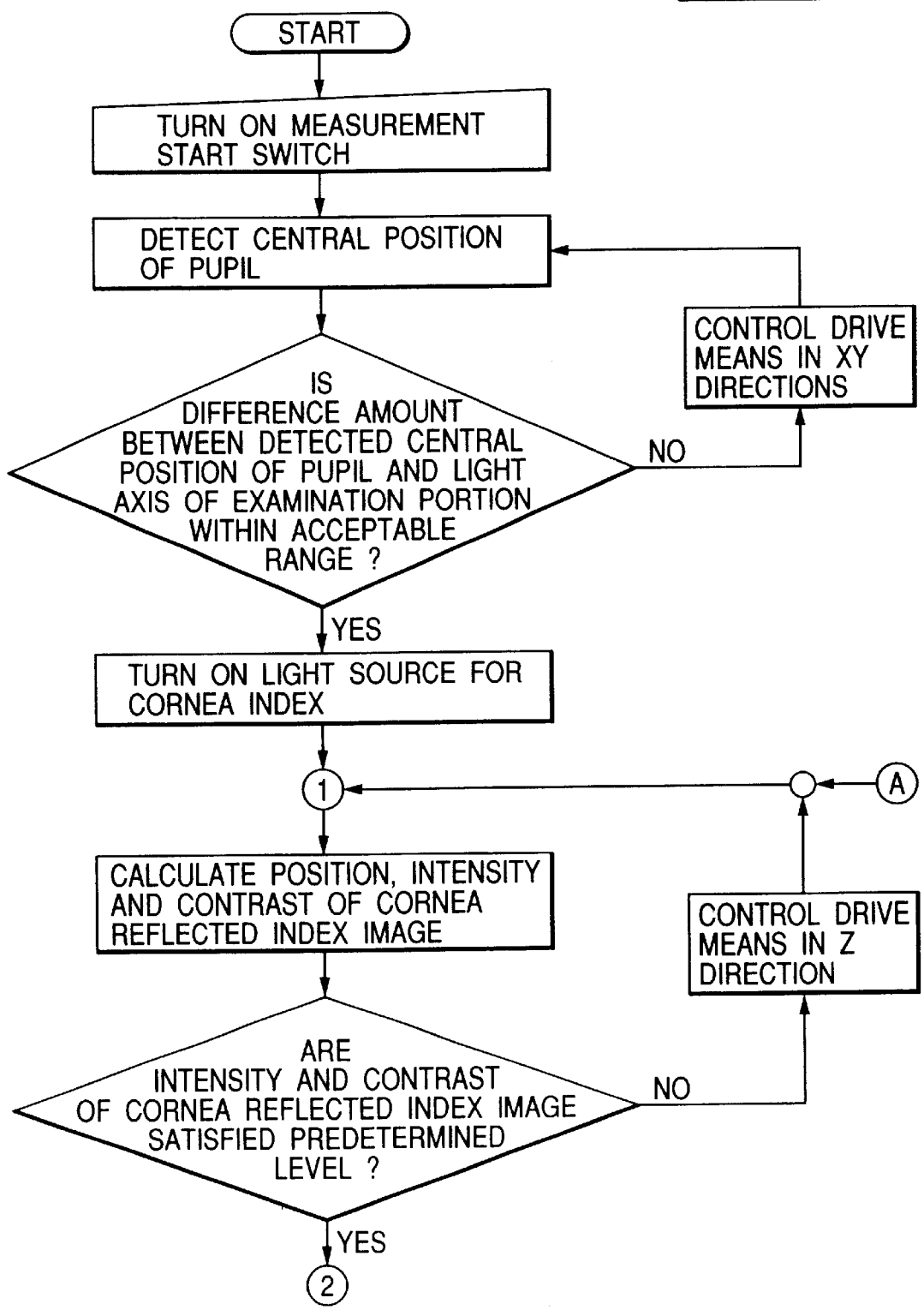
FIG. 2 is comprised of FIGS. 2A and 2B showing a flowchart to explain a computer processing procedure.
Figure 2B:
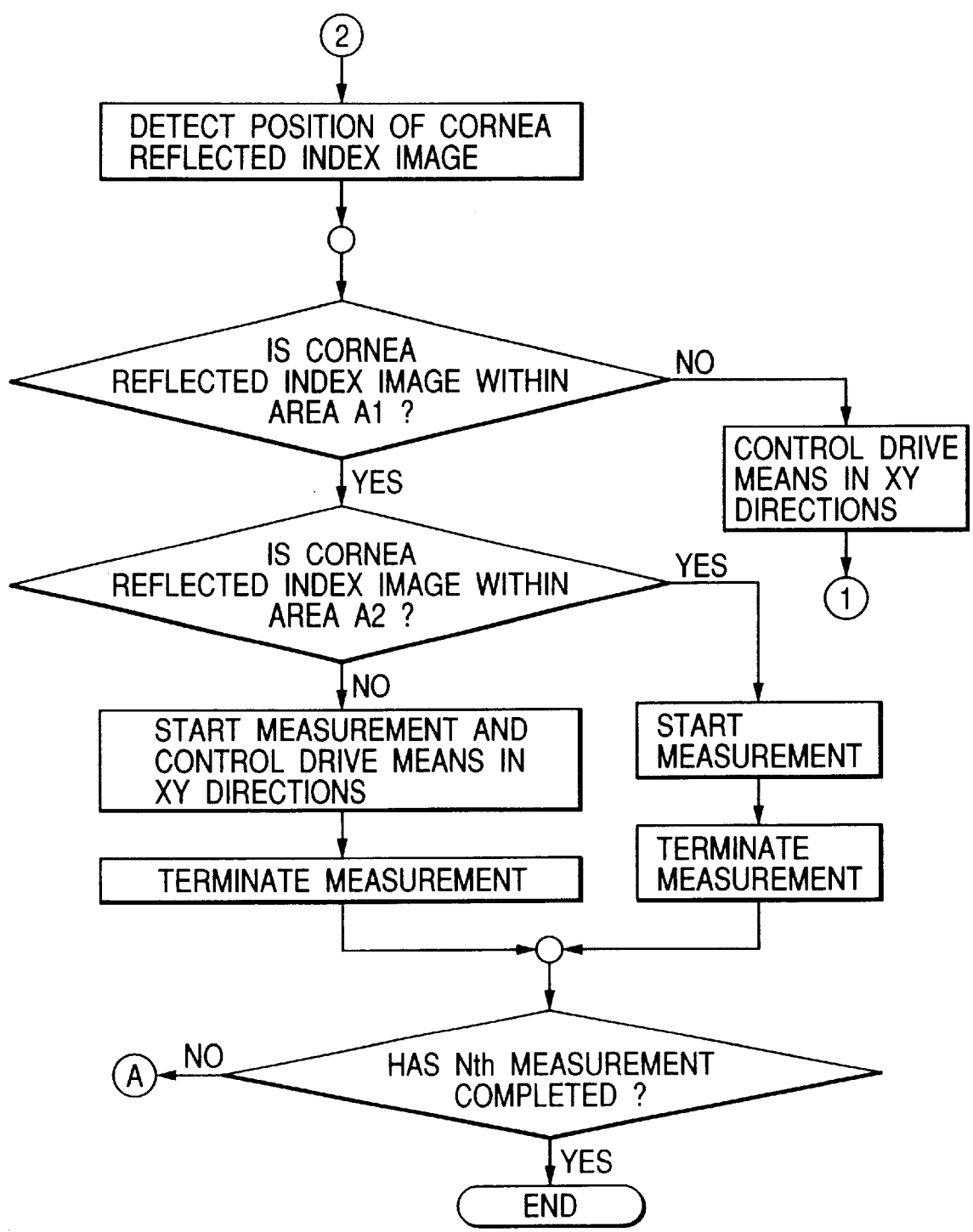

FIGS. 2A and 2B are flowcharts representing a processing procedure of the computer 28. When an examiner switches on a measurement start switch of the operation device 35, measurement operation is started and the illuminating light source 2 is turned on to illuminate the eye E. Reflected scattering light from the vicinity of the anterior eye part by the illuminating light source 2 is reflected by the dichroic mirror 1 and changed into approximately parallel light by the objection lens 3. The parallel light is reflected by the dichroic mirror 4 and passed through the dichroic mirror 5 and the imaging lens 6 to form an anterior eye part image on the image pickup device 7.

An output signal from the image pickup device 7 is converted into a digital signal by the A/D converter 25 and displayed as an anterior eye part image E' on the display unit 33 through the computer 28 and the D/A converter 32. Simultaneously, this digital signal is stored in the image memory 29. The computer 28 extracts a pupil from the anterior eye part image data stored in the image memory 29 to detect a center position of the pupil.

For example, when the anterior eye part is illuminated sufficiently to detect the center position of the pupil, the anterior eye part image becomes darkest in the pupil and light in the iris and the sclera sequentially. Thus, the center position of the pupil can be detected by binary coded processing using a suitable threshold with respect to a boundary of light in the pupil.

The computer 28 calculates a difference amount between the center position of the pupil and an optical axis of the examination unit in an X-Y plane, that is, plane vertical to the optical axis of the examination unit, after the center position of the pupil is detected, and controls the actuator 34 such that this difference amount becomes zero. After the center position of the pupil is detected and the actuator 34 is controlled, the computer 28 detects the center position of the pupil again, and determines whether a difference amount is within a preset acceptable range or not. When the difference amount is not within the acceptable range, the computer 28 performs X-Y control of the actuator 34 such that the difference amount becomes zero, and determines again whether a difference amount is within the acceptable range or not.

When the difference amount is within the acceptable range, the computer 28 turns on the index light source 24 immediately, and calculates a position, an intensity and a contrast of an index image. In this time, a light flux emitted from the index light source 24 illuminates the index plate 23. An index light flux passed through a transmitting portion of the index plate 23 is passed through the projection lens 22. Here, an image of the index plate 23 is formed at once by the beam splitter 12 before the objective lens 11. The light flux is changed into approximately parallel light by the objective lens 11. Most of the parallel light is passed through the dichroic mirror 1 and incident to the eye E.

A light flux reflected from a cornea Ec of the eye E forms a reflected image of a reflecting light flux in a middle position between the center of curvature of the cornea and a peak thereof. A portion of the light flux is reflected by the dichroic mirror 1, changed into approximately parallel light by the objective lens 3, deflected on the optical path 02 by the dichroic mirror 4, reflected by the dichroic mirror 5, and picked as an image including an index image in the image pickup device 9 through the imaging lens 8.

A signal from the image pickup device 9 is digitized by the A/D converter 26. This signal is stored in the image memory 30 and inputted to the computer 28 simultaneously. The computer 28 extracts an index image from image data including the index image stored in the image memory 30 to calculate a position, an intensity and a contrast of the index image. Then, the computer 28 detects difference amounts in the X and Y directions based on a relative position of the index image and a relative position in the Z-direction based on the intensity and the contrast of the index image.

The index image reflected from the cornea can be extracted by the following method. That is, since the index image is within the pupil commonly, among the image data including the index image, the pupil image is darkest and the index image is lightest. Thus, since the center position of the pupil has been detected, by searching a luminance point having a predetermined level or greater near the center position of the pupil from the image data, the index image can be easily specified, and its position, intensity and contrast can be calculated.

When the index image is calculated, it is determined that whether its intensity and contrast are satisfied with predetermined levels or not. When these are not satisfied with the predetermined levels, the Z-direction control of the actuator 34 is performed so as to satisfy these with the predetermined levels. After the calculation of intensity and contrast and the Z-direction control of the actuator 34 are completed at a first time, the calculation of intensity and contrast and the control of the actuator 34 are repeated until these is satisfied with the predetermined levels. Thus, an operation distance necessary to measure the distance between the examination unit and the eye E can be obtained.

Figure 3:
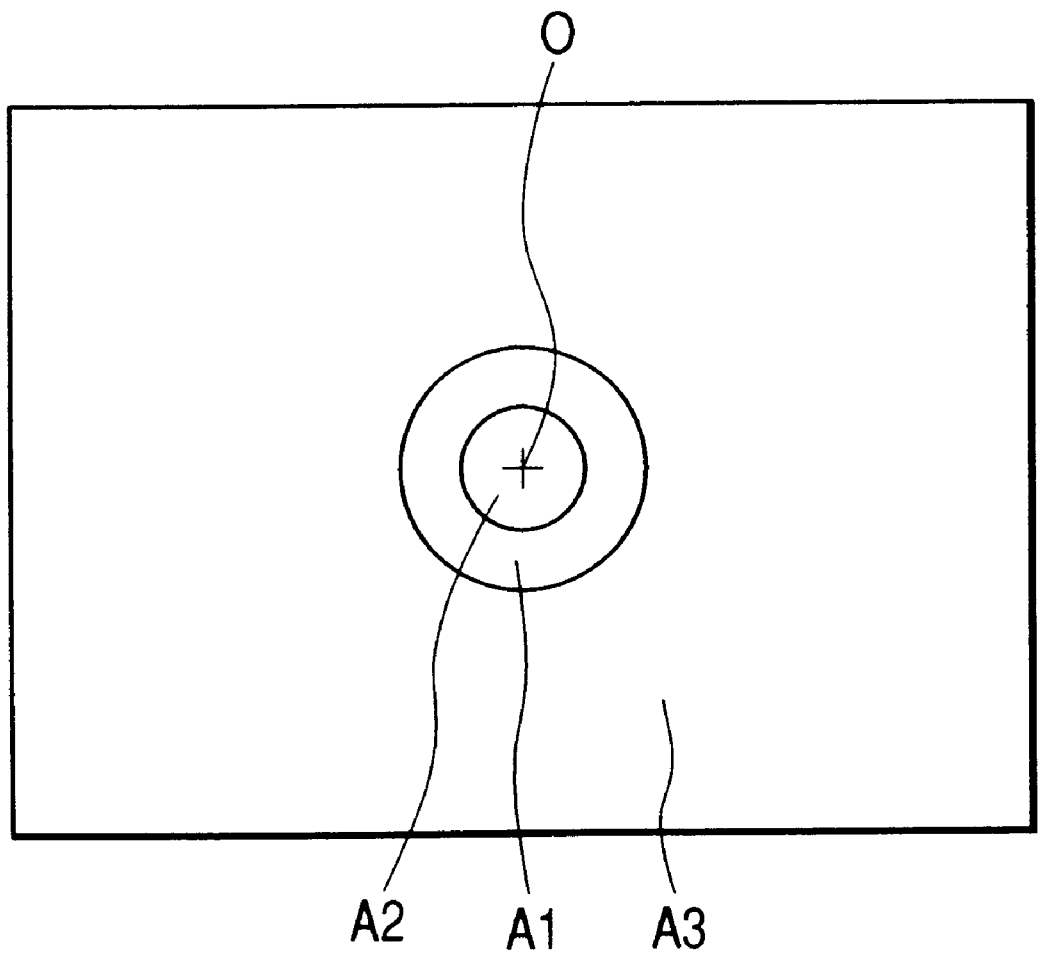
FIG. 3 is an explanatory diagram of an alignment processing procedure.

Here, as shown in FIG. 3, acceptable areas A1, A2 and A3 for alignment between a standard position of the eye E and the examination unit are divided concentrically, and these acceptable areas A1 to A3 are provided in a plane vertical to the measurement optical axis O in contact with a vertex of the cornea of the eye E when the eye E is in a suitable position. The area A1 is an area for controlling the actuator 34 so as to allow the measurement as well as align the optical axis O of the examination unit with the standard position of the eye E. The area A2 is provided within the area A1 and is an area for a processing procedure to allow the measurement. The area A3 is provided outside the areas A1 and A2, and is an area for controlling the actuator 34 so as to align the optical axis O of the examination unit with the standard position of the eye E.

Here, since a measurement value is varied somewhat depending on a relative position between the standard position of the eye E and the optical axis O of the examination unit, it is necessary to set the area A1 into an area that the measurement value can be obtained with a predetermined precision. Also, the areas A1 and A2 is preferably displayed on the display unit 33. Further, although the areas A1 and A2 are divided concentrically, these areas are not limited to concentric division, but for example, may be divided rectangularly.

Next, using the detected position of the index image as the standard position of the eye E, the computer 28 determines where the standard position of the eye E is within the areas A1 to A3. When the standard position of the eye E is determined to be within the area A1, since the standard position of the eye E is located in an end of an area that a predetermined measurement precision can be obtained, it may be located outside the area A1 depending on a little movement of an eye ball or the like. Thus, the computer 28 starts a measurement of eye refractive power by a known method immediately. Simultaneously, the computer 28 calculates a difference amount between the detected standard position of the eye E and the optical axis O of the examination unit, and performs the X-Y direction control of the actuator 34 so that the difference amount becomes zero.

Using a switch of the operation device 35, the number of measurements can be set arbitrarily. For example, if the number of measurements is set to be N times in advance or by an examiner, the computer 28 determines whether the number of measurements reaches N times or not, at the time when a first measurement is completed. When the number of measurements does not reach N times, the Z-direction control of the actuator 34 is performed again based on the intensity and the contrast of the index image, and then it is determined where the standard position of the eye E is within the areas A1 to A3 based on the position of the index image.

When the standard position of the eye E is within the area A2, since the standard position of the eye E is located in the vicinity of the center of an area that a predetermined measurement precision can be obtained, it is not located outside the area A2 depending on a little movement of an eye ball or the like. Also, it is not necessary to control the actuator 34 so as to align the optical axis O of the examination unit with the standard position of the eye E. Thus, the computer 28 starts a measurement of eye refractive power by a known method immediately. Also, the computer 28 controls the actuator 34 to perform a second measurement, similar to the case where the standard position of the eye E is within the area A1 after the first measurement is completed.

When the standard position of the eye E is within the area A3, the computer 28 calculates a difference amount between the standard position of the eye E and the optical axis O of the examination unit and performs the X-Y direction control of the actuator 34 such that the difference amount becomes zero. Then, the Z-direction control of the actuator 34 is performed again based on the intensity and the contrast of the index image, it is determined that the standard position of the eye E is within which of the areas A1 to A3 based on the position of the index image, and the actuator 34 is controlled in accordance with the areas A1 to A3.

After completion of the Nth measurement, if measurement of the other eye is not completed, measurement operation of the other eye is started automatically and then the predetermined number of measurements are performed. If measurement of the other eye is completed, a measurement result is displayed on the display unit 33 or printed in a printer (not shown) and then the entire measurement operation is completed.

As described above, in this embodiment, the standard position of the eye E is detected, a processing procedure for alignment between the standard position of the eye E and the examination unit is divided in accordance with a plurality of areas A1 to A3, and it is determined that the detected standard position of the eye E is within which of the areas A1 to A3, whereby a control method for measurement and alignment is changed. Thus, unnecessary control of the actuator 34 is not performed, and stable measurement can be performed quickly by minimum control.

Although the standard position of the eye E is calculated based on the index image, a center position of the pupil is calculated based on the pupil image instead of the index image and the calculated center position may be used as the standard position of the eye E.

Also, although the measurement light source 17 is separated from the index light source 24, by removing the beam splitter 12, the projection lens 22, the index plate 23 and the index light source 24, the measurement light source 17 may be used also as the index light source. Further, when the index image is detected commonly using the objective lens 3, the dichroic mirrors 4 and 5, the imaging lens 6 and the image pickup device 7 in the observing optical system, instead of the dichroic mirror 5, the imaging lens 8 and the image pickup device 9 in the index image pickup optical system, the apparatus can be simplified and miniaturized.

The index plate 23 is disposed on an optical axis. However, a plurality of cornea indexes are disposed outside the optical axis in symmetrical to the optical axis, and a plurality of index images are detected by the plurality of cornea indexes, whereby a center position of the plurality of index images may be used as the standard position of the eye E.

Second Embodiment

Figure 4:
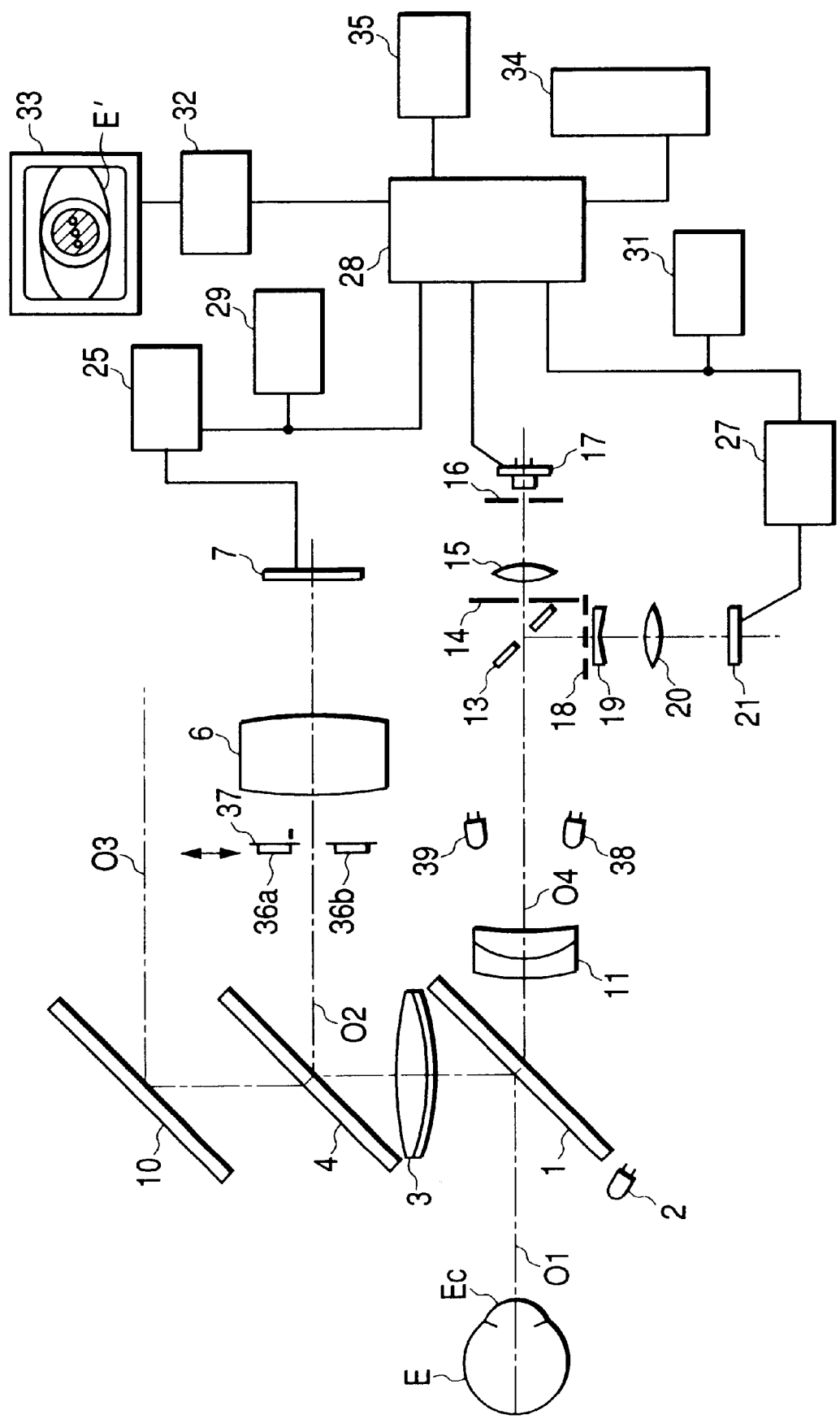
FIG. 4 shows an optical structure according to a second embodiment.

FIG. 4 shows an optical structure according to a second embodiment of the present invention. The dichroic mirror 5, the imaging lens 8 and the image pickup device 9 in the first embodiment are removed. A stop plate 37 having deflection prisms 36a and 36b is disposed on the optical path 02. Instead of the beam splitter 12, the lens 22, the index plate 23 and the index light source 24 in the first embodiment, index light sources 38 and 39 such as a light emitting diode, are disposed symmetrically on the optical path 04, whereby a projecting optical system for a cornea index which is co-operated with the objective lens 11 is constructed.

Figure 5:
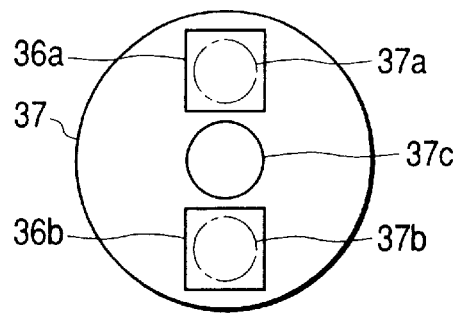
FIG. 5 is a front view of a stop plate having a deflection prism.

As shown in FIG. 5, two apertures 37a and 37b located symmetrically outside the optical axis and an aperture 37c located on the optical axis are formed in the stop plate 37. The deflection prisms 36a and 36b are located close to the apertures 37a and 37b, respectively. The index light sources 38 and 39 emit light having a wavelength which is different from a wavelength of light emitted from the illuminating light source 2 and similar to a wavelength of light emitted from the measurement light source 17. The apertures 37a and 37b of the stop plate 37 are constructed to transmit only light having a wavelength emitted from the measurement light source 17 and the index light sources 38 and 39. The deflection prism 36a is constructed to deflect a light flux in a back side to a plane of the Drawing sheet, and the deflection prism 36b is constructed to deflect a light flux in a front side to the plane of the Drawing sheet.

For example, the light flux emitted from the index light source 39 is projected to the cornea Ec of the eye E through the objective lens 11. The light flux reflected from the cornea Ec is deflected divisionally by the deflection prisms 36a and 36b and the stop plate 37 through the dichroic mirror 1, the objective lens 3 and the dichroic mirror 4 and led to the image pickup device 7 through the imaging lens 6.

Figure 6:
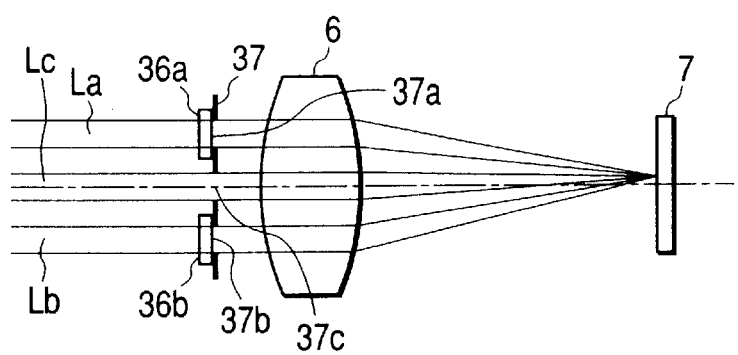
FIG. 6 is an explanatory diagram of a cornea reflected index light flux in the case where a position of an examination unit is suitable.
Figure 7:
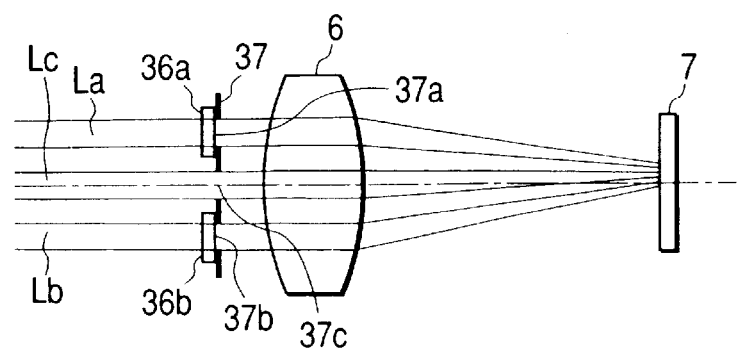
FIG. 7 is an explanatory diagram of a cornea reflected index light flux in the case where the examination unit is too near to the eye.
Figure 8:
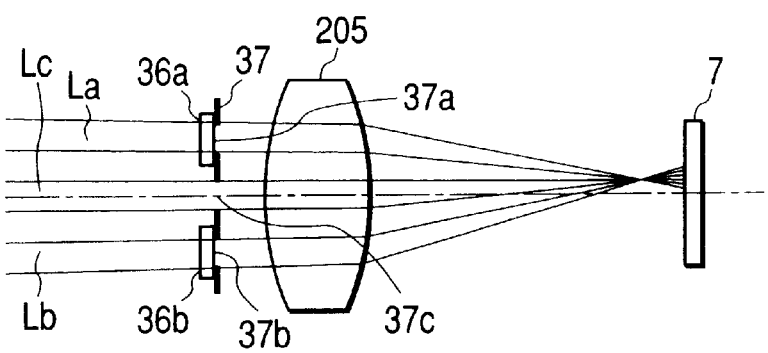
FIG. 8 is an explanatory diagram of a cornea reflected index light flux in the case where the examination unit is too far from the eye.

Here, FIGS. 6 to 8 represent states that a light flux emitted from the index light source 39 is led to the image pickup device 7 through the deflection prisms 36a and 36b, the stop plate 37 and the imaging lens 6. FIG. 6 shows the case where the examination unit to the eye E is located in a suitable position, FIG. 7 shows the case where the examination unit is too near to the eye E, and FIG. 8 shows the case where the examination unit is too far from the eye E. A light flux La is limited by the aperture 37a of the stop plate 37 and deflected by the deflection prism 36a in a back side to the plane of the Drawing sheet. A light flux Lb is limited by the aperture 37b and deflected by the deflection prism 36b in a front side to the plane of the Drawing sheet. A light flux Lc is limited by the aperture 37c.

Figure 9:
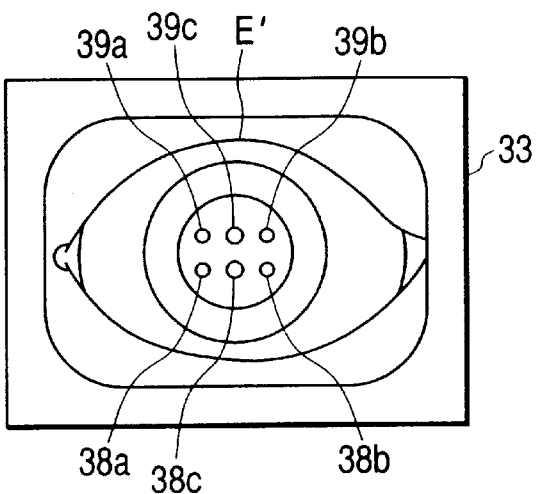
FIG. 9 is a front view of an anterior eye part image in the case where the examination unit is suitable.
Figure 10:
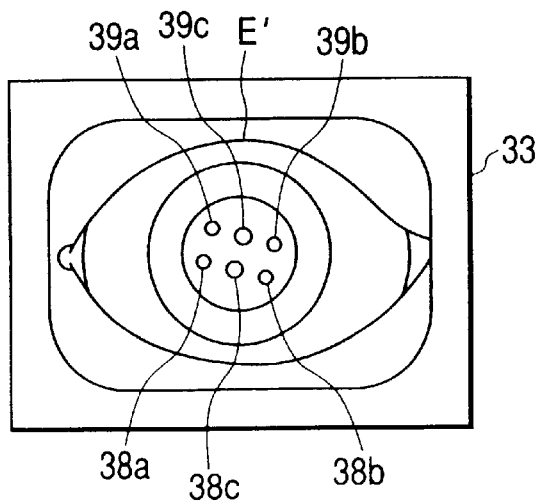
FIG. 10 is a front view of an anterior eye part image in the case where the examination unit is too near to the eye.
Figure 11:
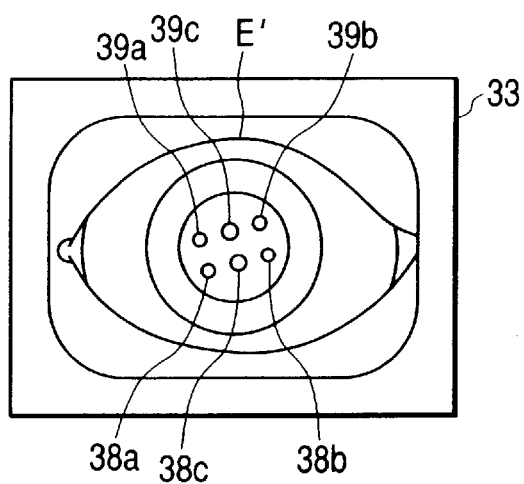
FIG. 11 is a front view of an anterior eye part image in the case where the examination unit is too far from the eye.

FIGS. 9 to 11 show an anterior eye part image E' displayed on the display unit 33 after the examination unit is aligned with a center position of the pupil. Images 38a, 38b and 38c represent index light source images obtained by dividing a light flux from the index light source 38 by the apertures 37a, 37b and 37c of the stop plate 37. Images 39a, 39b and 39c represent index light source image obtained by dividing a light flux from the index light source 39 by the apertures 37a, 37b and 37c of the stop plate 37. FIG. 9 shows the case where the examination unit to the eye E is located in a suitable position, FIG. 10 shows the case where the examination unit is too near to the eye E, and FIG. 11 shows the case where the examination unit is too far from the eye E.

As described above, in the second embodiment, the index light fluxes are projected from the index light sources 38 and 39 to the cornea Ec of the eye E. The light fluxes La, Lb and Lc reflected from the cornea Ec of the eye E are divided by the deflection prisms 36a and 36b and the stop plate 37, and positions of the index light source images 38a, 38b, 38c, 39a, 39b and 39c are detected, whereby a relative position between the eye E and the examination unit can be detected three-dimensionally. Thus, the examination unit can be aligned with the eye E suitably by controlling the actuator 34. Also, since the index light sources 38 and 39 are disposed symmetrically on the optical path 04, positions of the index light source images 38c and 39c which are located in the center, reflected from the cornea Ec of the eye E are detected, and then the center of the cornea Ec is calculated based on the middle point of these positions. Thus, the calculated center of the cornea Ec can be used as the standard position of the eye E.

Figure 12:
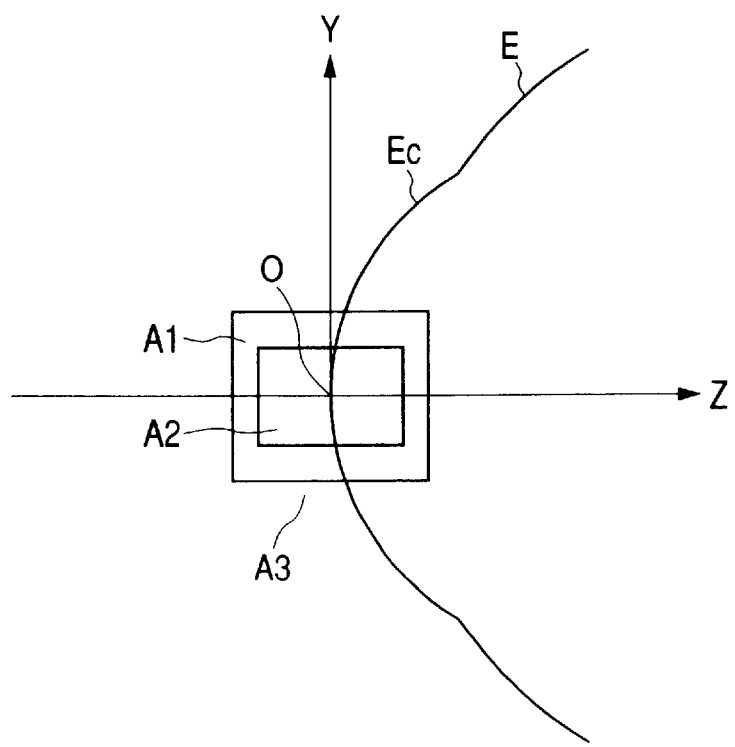
FIG. 12 is an explanatory diagram of a three-dimensional alignment processing procedure.

In the second embodiment, since the index light fluxes are projected from the index light sources 38 and 39 to the cornea Ec of the eye E and the index images are divided by the deflection prisms 36a and 36b and the stop plate 37, relative positions of three-axes between the standard position of the eye E and the examination unit can be detected. Thus, the areas for alignment between the standard position of the eye E and an eye examination portion can be divided corresponding to the processing procedures A1 to A3 as shown in FIG. 12. These areas A1 to A3 are an area when the examination unit on a Y-Z plane including the Z-axis as the optical axis O of the examination unit and the Y-axis vertical to the Z-axis is aligned in a suitable position with respect to the eye E.

In this case, the optical axis O is used as a standard for aligning the examination unit with the standard position of the eye E. The areas A1 and A2 are a three-dimensional area having a rotation symmetric shape with the Z-axis as a rotation axis. The area A1 is an area for controlling the actuator 34 so as to allow the measurement and to align the optical axis O with the standard position of the eye E. The area A2 is provided within the area A1 and is an area for allowing the measurement. The area A3 is provided outside the areas A1 and A2 and is an area for controlling the actuator 34 so as to align the optical axis O with the standard position of the eye E.

Based on the above method, the computer 28 detects a relative position of the standard position of the eye E with respect to the examination unit and determines where the standard position of the eye E is within the areas A1 to A3, whereby a control method of the actuator 34 is changed similar to the first embodiment.

Therefore, a relative position between the standard position of the eye E and the examination unit is detected three-dimensionally. A processing procedure for alignment between the standard position of the eye E and the examination unit is divided three-dimensionally in accordance with the plurality of areas A1 to A3, and it is determined that the determined standard position of the eye E is within which of the areas A1 to A3, whereby a control method for measurement and alignment is changed based on the areas A1 to A3. Thus, unnecessary control of the actuator 34 is not performed, and stable measurement can be performed quickly by minimum control.

The ophthalmologic apparatus as described above divides a processing procedure for alignment between the standard position of the eye and a measurement system in accordance with the plurality of areas, determines that the standard position of the eye is within which of the plurality of areas, and changes a control method for at least one of the measurement system and the actuator based on the determined area. Thus, unnecessary control of the actuator is not performed, and stable measurement values can be obtained quickly. Also, when an index image detecting unit is constructed by commonly using the measurement light source and the index light source, and further commonly using the index image pickup optical system and the observing optical system, the apparatus can be simplified and miniaturized.

Third Embodiment

Figure 13:
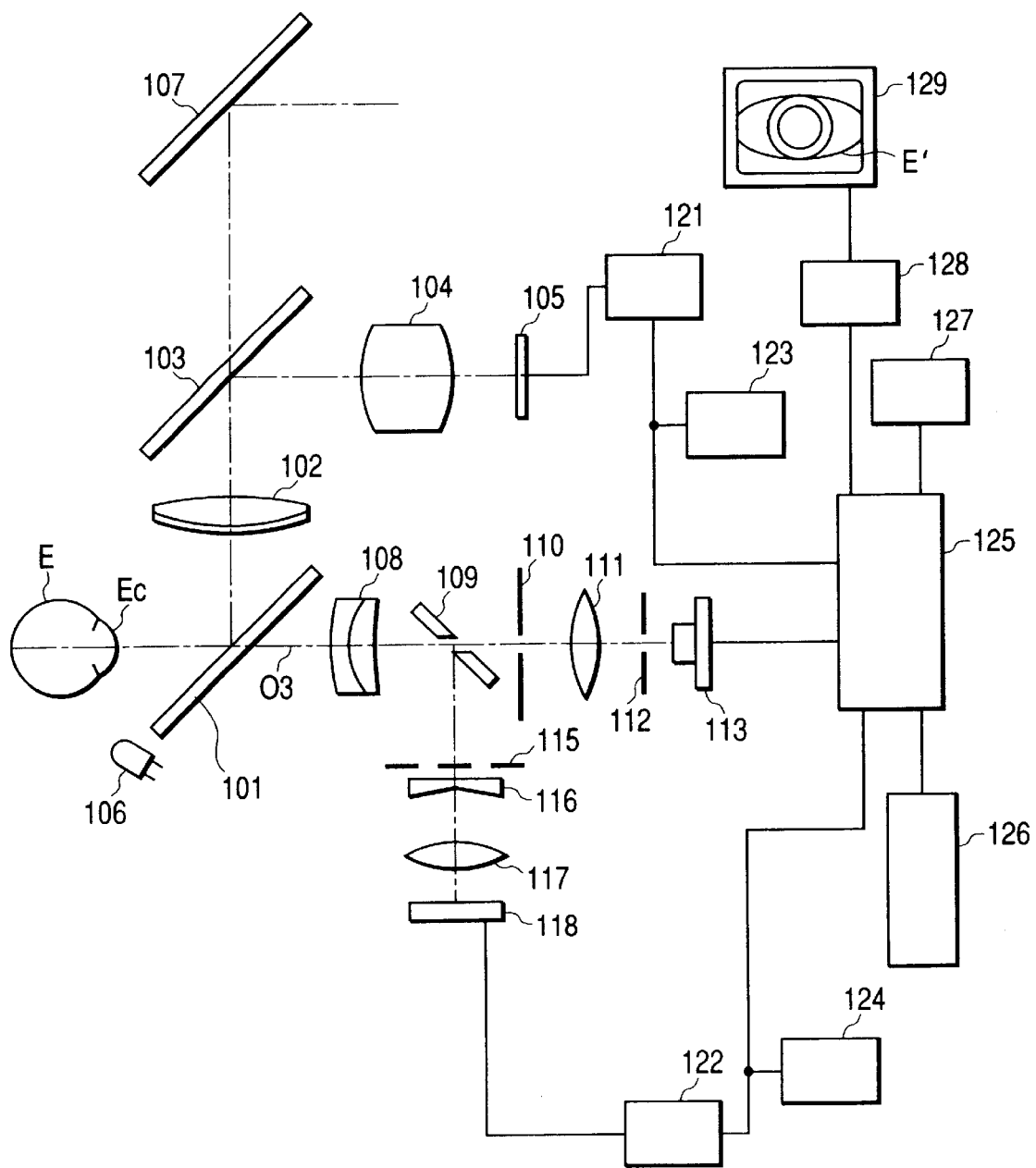
FIG. 13 shows an optical structure according to a third embodiment.

FIG. 13 shows a structure of an ophthalmologic apparatus according to a third embodiment. A dichroic mirror 101 is disposed opposite to the eye E. An objective lens 102 for observation and a dichroic mirror 103 are disposed in a reflecting direction of the dichroic mirror 101. An imaging lens 104 and an image pickup device 105 such as a CCD camera are disposed on the optical path 01 in a reflecting direction of the dichroic mirror 103. The image pickup device 105 is approximately conjugate with the vicinity of an anterior eye part. An illuminating light source 106 such as an LED for emitting near-infrared light to illuminate the anterior eye part is disposed in a position outside an optical path between the eye E and the dichroic mirror 101. An observing optical system is constructed by the objective lens 102, the dichroic mirror 103, the imaging lens 104, the image pickup device 105 and the illuminating light source 106.

A mirror 107 is disposed on the optical path 02 in a transmitting direction of the dichroic mirror 103. An projecting optical system (not shown) for a fixed index for fixing an eye is disposed in a reflecting direction of the mirror 107.

On the other hand, an objective lens 108 for measurement, a partial hole mirror 109, a projectile aperture 110, a projection lens 111, an index plate 112 and a measurement light source 113 for emitting near-infrared light having a wavelength longer than the illuminating light source 106 by several tens of nm are disposed on the optical path 03 in the transmitting direction of the dichroic mirror 101. A six holes aperture 115 having six holes outside an optical axis, a six divided prism 116, a relay lens 117 and an image pickup device 118 such as a CCD camera are disposed in the reflecting direction of the partial hole mirror 109. A projecting optical system for measurement light is constructed by the objective lens 108, the partial hole mirror 109, the aperture 110, the projection lens 111, the index plate 112 and the measurement light source 113. A receiving optical system for eye refractive power measurement is constructed by the objective lens 108, the partial hole mirror 109, the six holes aperture 115, the six divided prism 116, the relay lens 117 and the image pickup device 118.

Also, an examination unit having a plurality of optical systems mentioned above is constructed. This examination unit is mounted on a base movable in three axis directions. Operating a joystick by an examiner, the examination unit can be moved flexibly. An alignment mechanism is constructed by the base, the joystick and the like.

Here, the dichroic mirror 101 has a characteristic such that most of light of wavelength emitted from the measurement light source 113 are transmitted and a portion of the light is reflected and such that light of wavelength emitted from the illuminating light source 106 is reflected. Also, the dichroic mirror 103 has a characteristic such that visible light is transmitted and near-infrared light is reflected.

Outputs of the image pickup devices 105 and 118 are connected with A/D converters 121 and 122, respectively. Outputs of the A/D converters 121 and 122 are connected with image memories 123 and 124, respectively and further connected with a computer 125 for controlling the entire apparatus. The measurement light source 113, an operation device 126 in which a switch for starting measurement, a switch for displaying an alignment mark, which is described later and the like are arranged, and a character generator 127 are connected with the computer 125. An output of the computer 125 is connected with a display unit 129 through a D/A converter 128.

Figure 14:
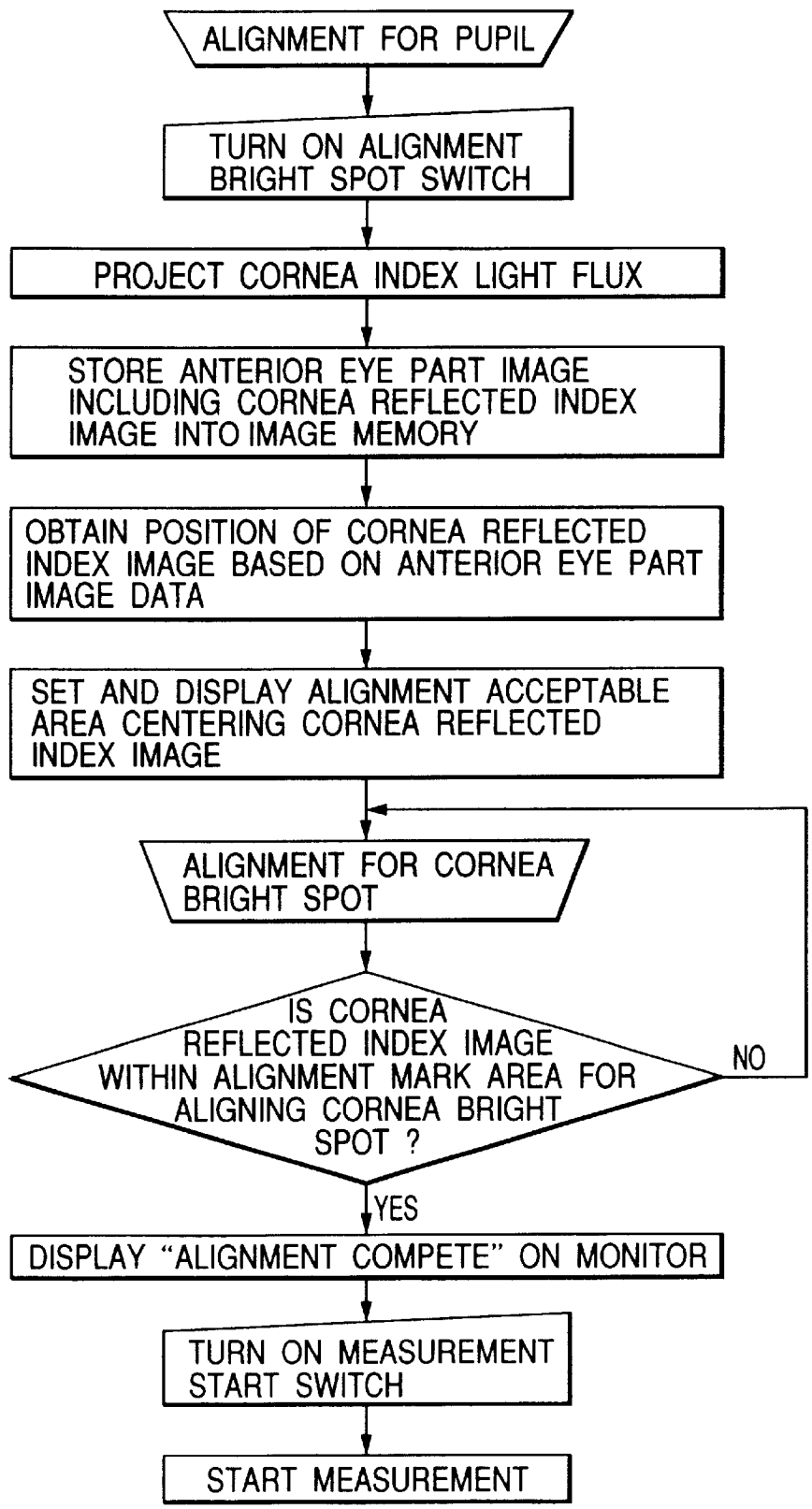
FIG. 14 is a flowchart.

FIG. 14 shows a flowchart representing an operation of the embodiment. The eye E is illuminated by the illuminating light source 106. Reflected scattering light from the vicinity of the anterior eye part is reflected by the dichroic mirror 101 and changed into approximately parallel light by the objective lens 102. The parallel light is reflected by the dichroic mirror 103 and imaged on the image pickup device 105 by the imaging lens 104. An output signal from the image pickup device 105 is converted into a digital signal by the A/D converter 121 and displayed as an anterior eye part image E' on the display unit 129 through the computer 125 and the D/A converter 128.

Figure 15:
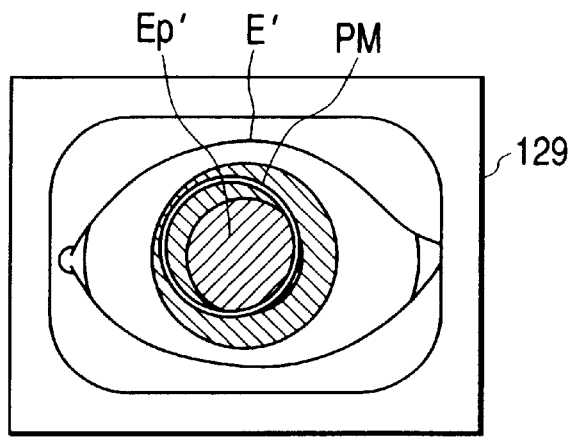
FIG. 15 is an explanatory diagram of an anterior eye part image and an alignment mark.
Figure 16:
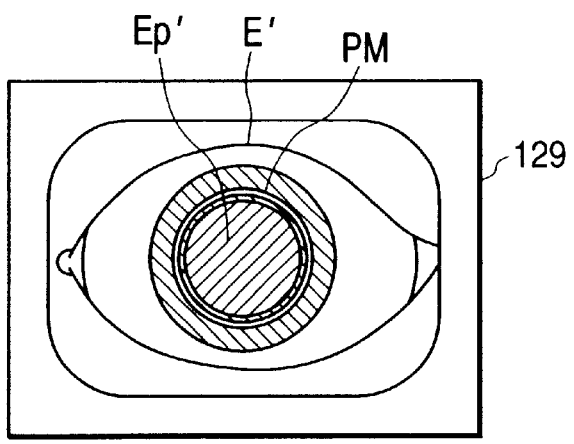
FIG. 16 is an explanatory diagram of the case where the eye pupil image and the alignment mark become a concentric state.

While observing the anterior eye part image E' displayed on the display unit 129, an examiner operates the alignment mechanism constructed by a base, a joystick and the like to actuate the examination unit in three directions (up and down, right and left, front and back), so that alignment between the eye E and the examination unit is performed. After rough alignment between the eye E and the examination unit as shown in FIG. 15 is completed, the examiner operates the alignment mechanism such that a pupil image Ep' of the eye E and an alignment mark PM for pupil alignment displayed on the display unit 129 become a concentric circle, as shown in FIG. 16. This alignment mark PM is generated by the character generator 127, synthesized through the computer 125, and displayed together with the pupil image Ep' on the display unit 129.

As shown in FIG. 16, when the alignment is completed, it is required that the examiner operates the alignment mechanism in accordance with movement of the eye E so as to keep a relative position to the eye E constant, during measurement, whereby the apparatus is needed to be actuated in three directions (up and down, right and left, front and back). In this embodiment, the apparatus can be actuated easily in accordance with the movement of the eye E.

The examiner observes the display unit 129 and operates the alignment mechanism. Then, after the pupil image Ep' and the alignment mark PM become a concentric circle, as shown in FIG. 16, when the examiner pushes the switch for displaying the alignment mark provided in the operation device 126, the computer 125 turns on the measurement light source 113.

The index plate 112 is illuminated with light emitted from the measurement light source 113. A light flux limited by the index plate 112 is passed through the projection lens 111 and the projectile aperture 110, imaged on a focal surface of the objective lens 108 at once, and changed into parallel light by the objective lens 108. Most of the parallel light flux is passed through the dichroic mirror 101 and reaches the eye E. A light flux reflected from the cornea Ec of the eye E forms a reflected image of the reflecting light flux in a middle position between the center of curvature of the cornea and a vertex thereof. A portion of the light flux is reflected by the dichroic mirror 101, changed into approximately parallel light by the objective lens 102, deflected to the optical path 01 by the dichroic mirror 103, imaged on the image pickup device 105 by the imaging lens 104. A signal from the image pickup device 105 is displayed as a cornea reflected index image I on the display unit 129 through the A/D converter 121, the computer 125 and the D/A converter 128.

Figure 17:
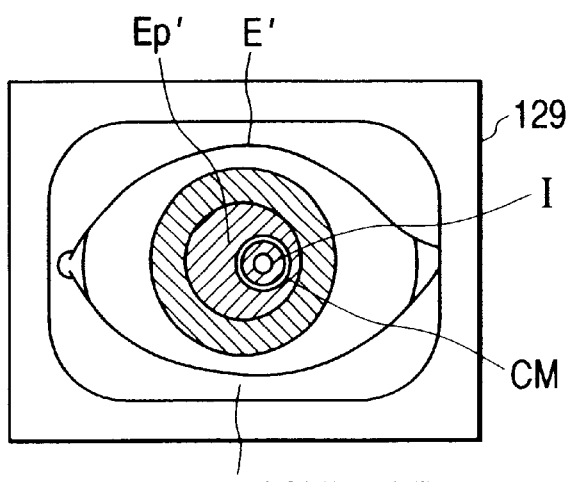
FIG. 17 is an explanatory diagram of an index image and an alignment mark for luminance point alignment to a cornea.

Simultaneously, the computer 125 extracts the cornea reflected index image I from image data including the cornea reflected index image I stored in the image memory 123 and calculates an address in a memory. Then, by the computer 125, the alignment mark CM for luminance point alignment to a cornea with a radius R predetermined in the center of the calculated address is generated by the character generator 127, as shown in FIG. 17, and displayed together with the cornea reflected index image I on the display unit 129 through the D/A converter 128.

The examiner operates the alignment mechanism in accordance with movement of the eye E such that the cornea reflected index image I is always within an area represented by the alignment mark CM. Since it is not necessary to perform alignment depending on a pupil whose size is changed by the adjustment of the eye E or the like, the apparatus can be further easily aligned in the center of a pupil.

Then, when a position of the eye E is shifted from that of the apparatus by an eye ball movement or the like, there is a case where the cornea reflected index image I is located outside the area. Thus, the computer 125 determines whether the cornea reflected index image I exists within the area or not. For example, when it exists within the area, a message alignment completed is displayed on the display unit 129 to inform the examiner of an alignment state.

After the message alignment completed is displayed on the display unit 129, when the measurement start switch provided in the operation device 126 is pushed by the examiner, the computer 125 causes the measurement light source 113 to emit light with an amount necessary for eye refractive power measurement. A light flux emitted from the measurement light source 113 is passed through the index plate 112, reaches the eye E as similarly described above, and is imaged as an index image on a fundus of the eye E. Most of the light reflected and scattered from the index image as a secondary light source is passed through the dichroic mirror 101, reflected by the partial hole mirror 109 through the objective lens 108, and divided into six light fluxes by the six holes aperture 115. Then, these light fluxes are formed as six spot images on the image pickup device 118 through the six divided prism 116 and the relay lens 117.

The image signals are converted into digital signals by the A/D converter 122 and stored in the image memory 124. The computer 125 calculates the eye refractive power of the eye E from the information stored in the image memory 124, and controls the projecting optical system (not shown) for a fixed index provided on the optical path 02, to prompt a person to be examined to fog. This operation is repeated several times. Thus, the eye refractive power of the eye E which is in a fogging state without adjustment can be measured.

As described in a conventional example, too, it is said that the center of a pupil of the human eye does not necessarily coincide with a vertex of a cornea thereof but rather these become eccentric in many cases. Thus, with respect to the eye E which eccentricity of the vertex of the cornea to the center of the pupil is large, when the alignment for a cornea vertex as a standard is performed, there is a fear that a light flux necessary to measure information inherent to the eye is shaded by the pupil. In this embodiment, since the alignment for such an eye is performed based on the index image I located in the vicinity of the cornea vertex and the optical axis of the apparatus is aligned with the center of the pupil, the light flux necessary for measurement is not shaded by the pupil.

In order to measure the eye refractive power with a high precision, as described above, it is required that the eye E is in a fogging state, so that a measurement time is needed somewhat. Therefore, in the embodiment, after measurement is started, the computer 125 detects whether the index image I is within the area represented by the alignment mark CM for the luminance point alignment to the cornea. When the index image I is not within the area, the computer 125 controls the apparatus so as to stop the measurement or to stop it temporarily. When the index image I is observed within the area again, the computer 125 may control the apparatus so as to restart the measurement.

Also, in this embodiment, as shown in FIG. 16, after the pupil Ep and the alignment mark PM become an approximately concentric circle, when the examiner pushes the alignment mark display switch provided on the operation device 126, the computer 125 turns on the measurement light source 113 and calculates a position of the index image I. Then, by the computer 125, the alignment mark CM for luminance point alignment to a cornea with a radius R predetermined around the calculated position is displayed together with the cornea reflected index image I on the display unit 129.

Observing the display unit 129, the examiner operates the alignment mechanism in accordance with movement of the eye E. When the index image I is within the alignment mark CM for the luminance point alignment to the cornea and the measurement start switch provided in the operation device 126 is pushed, information inherent to the eye E is measured.

The computer 125 may detect that the index image I is within the area representing the alignment mark CM for luminance point alignment to the cornea and start the measurement automatically. Or, the computer 125 may detect that the index image I is within the area representing the alignment mark CM for luminance point alignment to the cornea and inform the examiner of the detected result by using an indicator (for example, a message such as alignment completed displayed on the display unit 129 or a sound by such as a buzzer).

Further, in this embodiment, the alignment mark PM and the alignment mark CM for luminance point alignment to the cornea both are a circle. However, a shape of these alignment marks is not limited to a circle, if the center of the alignment marks PM and CM may be judged, the alignment mark having other shapes may be used to obtain the same operation.

As described above, in the ophthalmologic examination apparatus, by control so as to display the alignment mark representing a position of the index image around the index image on the display unit, the apparatus can be aligned easily with the center of the pupil of the eye in accordance with the eye ball movement. Also, since the alignment with the center of pupil is performed, a shade amount of a light flux necessary for measurement due to the pupil of the eye can be reduced, a stable eye examination can be performed, and an examination time can also be shortened.

Also, by detecting whether the index image is within the area represented by the alignment mark or not and using an indicator to inform the examiner of a detected result, the examiner can easily grasp an alignment state between the eye and the apparatus, with the result that, since the measurement can be performed after the alignment is completed, a stable eye examination can be performed.

Further, by detecting whether the index image is within the area represented by the alignment mark or not and automatically measuring the eye inherent information with respect to the predetermined number of measurements in the case where the index image is within the area, the examiner can examine easily the eye by operation with only alignment between the eye and the apparatus.

Furthermore, by detecting whether the index image is within the area represented by the alignment mark or not and automatically stopping the measurement of the eye inherent information in the case where the index image is not within the area, since the measurement in an insufficient alignment state can be avoided, a stable eye examination result can be obtained.

By detecting whether the index image is within the area represented by the alignment mark or not, automatically stopping the measurement of the eye inherent information in the case where the index image is not within the area, and then automatically restarting the measurement of the eye inherent information in the case where the index image is within area, since the measurement in an insufficient alignment state can be avoided and the measurement can be restarted automatically in the case where the alignment state is suitable, a stable eye examination result can be obtained and an examination time can also be shortened.

Fourth Embodiment

Figure 18:
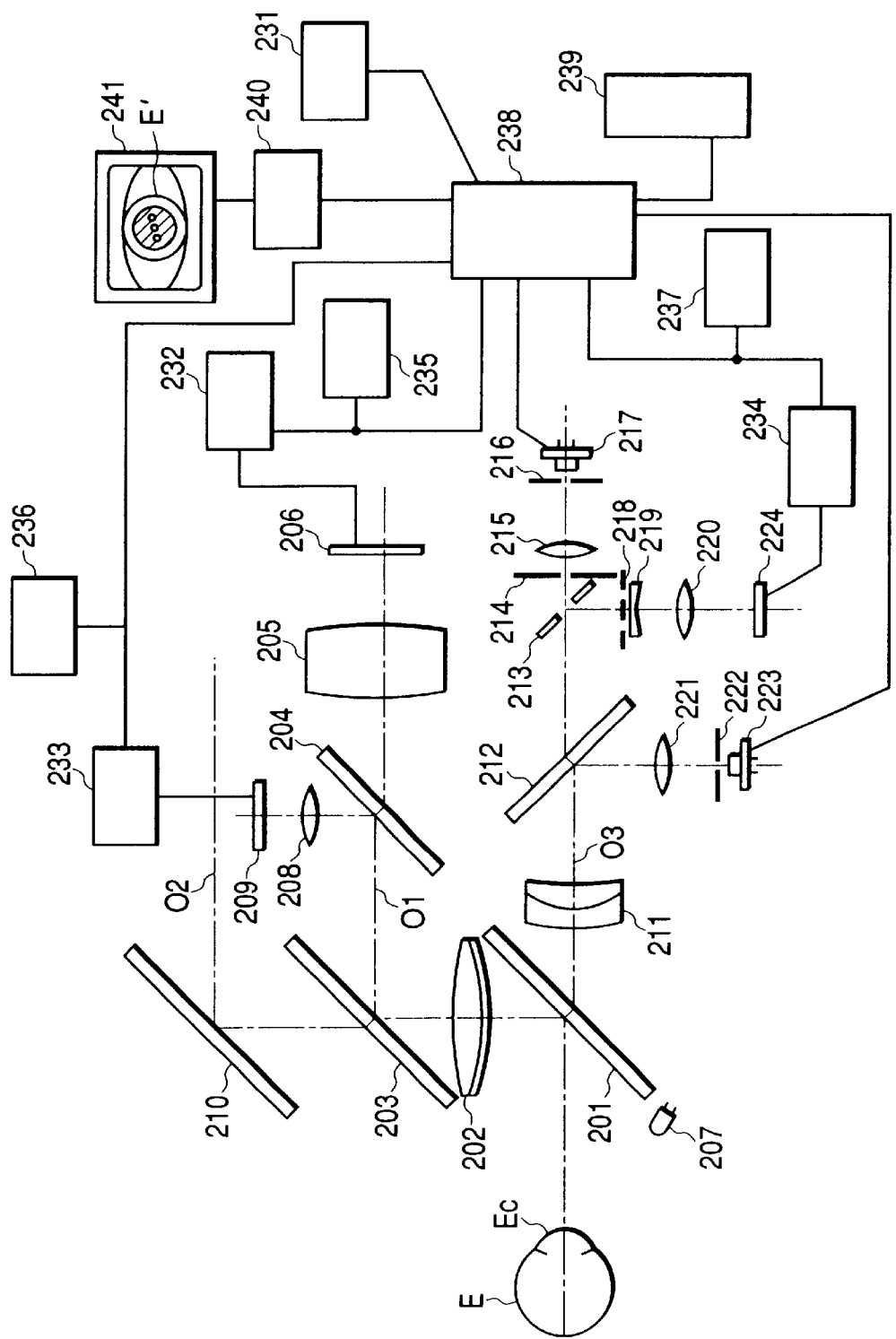
FIG. 18 shows an optical structure according to a fourth embodiment.

FIG. 18 shows a structure of the ophthalmologic apparatus according to a fourth embodiment. A dichroic mirror 201 is disposed opposite to the eye E. A lens 202 and a dichroic mirror 203 are disposed in a reflecting direction of the dichroic mirror 203. A dichroic mirror 204 and an imaging lens 205 are provided on the optical path 01 in a reflecting direction of the dichroic mirror 203. An image pickup device 206 such as a CCD camera is disposed in a position approximately conjugate with the vicinity of an anterior eye part. An illuminating light source 207 an LED for emitting near-infrared light to illuminate the anterior eye part is disposed in a position outside an optical axis between the eye E and the dichroic mirror 201. An observing optical system is constructed by the lens 202, the dichroic mirror 203, the imaging lens 205 and the image pickup device 206.

Also, an imaging lens 208 and an image pickup device 209 such as a CCD camera are in a reflecting direction of the dichroic mirror 204. The image pickup device 209 is located in a position approximately conjugate with the vicinity of the anterior eye part. An index image pickup optical system is constructed by the lens 202, the dichroic mirrors 203 and 204, the imaging lens 208 and the image pickup device 209.

A mirror 210 is disposed on the optical path 02 in a transmitting direction of the dichroic mirror 203. An projecting system (not shown) for a fixed index for fixing the eye E is disposed in a reflecting direction of the mirror 210. On the other hand, an objective lens 211 for measurement, a beam splitter 212 such as a half mirror, a partial hole mirror 213, an aperture 214, a projection lens 215, an index plate 216 and a measurement light source 217 for emitting near-infrared light having a wavelength of several tens of nm longer than the illuminating light source 207 are disposed on an optical path 03 in a transmitting direction of the dichroic mirror 201. A projecting optical system for eye refractive power measurement is constructed by the objective lens 211, the beam splitter 212, the partial hole mirror 213, the aperture 214, the projection lens 215, the index plate 216 and the measurement light source.

Also, a six hole stop 218 having six holes outside an optical axis is disposed in a reflecting direction of the partial hole mirror 213. A six divided prism 219, a relay lens 220 and an image pickup device 224 such as a CCD camera are disposed in a back side of the six holes aperture 218. A receiving optical system for eye refractive power measurement is constructed by the objective lens 211, the beam splitter 212, the partial hole mirror 213, the six holes aperture 218, the six divided prism 219, the relay lens 220 and the image pickup device 224.

Further, a projection lens 221, a cornea index 222 and an index light source 223 an LED for emitting near-infrared light are disposed on an optical axis in a reflecting direction of the beam splitter 212. A projecting optical system for a cornea index is constructed by the objective lens 211, the beam splitter 212, the projection lens 221, the cornea index 222 and the index light source 223.

Here, the dichroic mirror 201 has a characteristic such that most of the light of wavelength emitted from the measurement light source 217 and the index light source 223 are transmitted and a portion of the light is reflected, and such that the light of wavelength emitted from the illuminating light source 207 is reflected. Also, the dichroic mirror 203 has a characteristic such that visible light is transmitted and the near-infrared light is reflected. The dichroic mirror 204 has a characteristic such that the light of wavelength emitted from the measurement light source 217 and the index light source 223 are reflected and the light of wavelength emitted from the illuminating light source 207 is transmitted.

An examination unit is constructed by a plurality of optical systems mentioned above. This examination unit is mounted on a base movable in three axis directions. The base is movable electrically by an actuator 231 such as a motor.

The image pickup devices 206, 209 and 224 are connected with A/D converters 232, 233 and 234, respectively. Outputs of the A/D converters 232, 233 and 234 are connected with image memories 235, 236 and 237, respectively, and further connected with a computer 238 for controlling the entire apparatus. The measurement light source 217, the index light source 223, and an operation device 239 in which a measurement start switch, a switch for operating an actuator and the like are arranged are connected with the computer 238. Also, a D/A converter 240, a display unit 241 and the actuator 231 are connected with the computer 238.

Figure 19:
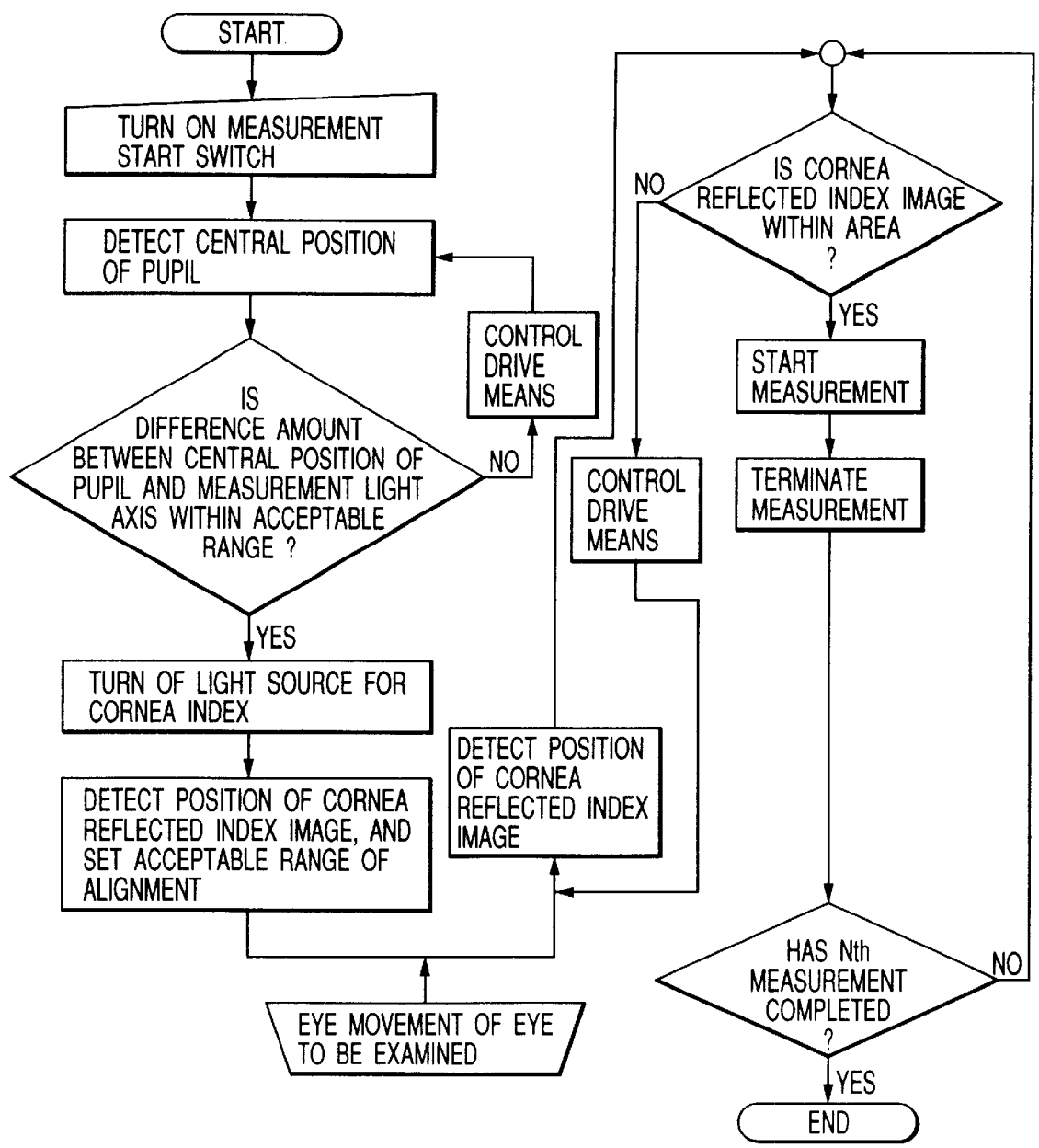
FIG. 19 is a flowchart.

FIG. 19 shows a flowchart representing an operation of this embodiment. When an examiner pushes the measurement start switch provided in the operation device 239, the apparatus starts measurement operation. Then, the eye E is illuminated by the illuminating light source 207. Reflected scattering light from the vicinity of the anterior eye part of the eye E due to the illuminating light source 207 is reflected by the dichroic mirror 201 and changed into approximately parallel light by the objective lens 202. The parallel light is reflected by the dichroic mirror 203, transmitted through the dichroic mirror 204, and is imaged on the image pickup device 206 through the imaging lens 205.

An output signal from the image pickup device 206 is converted into a digital signal by the A/D converter 232 and displayed as an anterior eye part image E' on the display unit 241 through the computer 238 and the D/A converter 240. Simultaneously, when the anterior eye part image data converted into the digital signal is stored in the image memory 235, the computer 238 extracts a pupil from the anterior eye part image data stored in the image memory 235 to detect a center position of the pupil.

A method for detecting the center position of the pupil is as follows. For example, when the anterior eye part is illuminated sufficiently, the anterior eye part image E' becomes darkest in the pupil and light in the iris and the sclera sequentially. Thus, a boundary of the pupil can be obtained by binary coded processing using an appropriate threshold value, so that the center position of the pupil can be calculated.

When the center position of the pupil is detected, the computer 238 calculates a difference amount between an optical axis of the examination unit and the center position of the pupil in a plane vertical to the optical axis of the examination unit, and controls the actuator 231 such that this difference amount becomes zero. After the center position of the pupil is detected and the actuator 231 is controlled at a first time, the computer 238 detects the center position of the pupil again, and determines whether a difference amount to a measurement optical axis of the apparatus is within a preset acceptable range or not.

When the difference amount is not within the acceptable range, the computer 238 controls the actuator 231 such that an optical axis of the examination unit is aligned with the center position of the pupil, and determines again whether a difference amount between the center position of the pupil and the measurement optical axis of the apparatus is within the acceptable range or not.

When the difference amount is within the acceptable range, the computer 238 turns on the index light source 223 immediately. Then, a light flux emitted from the index light source 223 illuminates the cornea index 222. An index light flux passed through a transmitting portion of the cornea index 222 is passed through the projection lens 221. Here, an image of the cornea index 222 is formed by the beam splitter 212 before the objective lens 211 at once. The light flux is changed into approximately parallel light by the objective lens 211. Most of the parallel light is passed through the dichroic mirror 201 and reaches the eye E.

A light flux reflected from the cornea Ec of the eye E forms a reflected image of the reflecting light flux in a middle position between the center of curvature of the cornea and a peak thereof. A portion of the light flux is reflected by the dichroic mirror 201, changed into approximately parallel light by the objective lens 202, deflected to the optical path 01 by the dichroic mirror 203, reflected by the dichroic mirror 204, imaged as an image including the index image on the image pickup device 209 by the imaging lens 208. A signal from the image pickup device 209 is digitized by the A/D converter 233 and stored in the image memory 236.

Simultaneously, the computer 238 extracts the index image from image data including the index image stored in the image memory 236 and sets an alignment acceptable area which has a predetermined size, with a position of the extracted index image as the center. The predetermined size of the alignment acceptable area is set by precalculating a range in which stable measurement values are obtained in the case where eye inherent information is measured. The alignment acceptable area may be displayed on a TV monitor or the like.

Next, by using a known method, the projecting optical system for a fixed index is controlled to prompt fogging of the eye E. For further accuracy refractive measurement of the eye E, it is necessary to prompt the fogging by keeping the fixed index away from the eye stepwise. Also, a time for adjusting the eye E for several seconds is required. Here, as described above, in the case where the fogging of the eye E is prompted after an alignment acceptable area with a position of the index image as the center is set while the center position of the pupil is detected, it is aligned with the measurement optical axis of the apparatus, and the position of the index image is simultaneously detected, the index image may be located outside the set alignment acceptable area by eye ball movement of the eye E or the like. That is, it is presented that a difference amount between the center of the pupil and the measurement optical axis of the apparatus is not within a measurement acceptable area.

When the eye E is in a fogging state, the computer 238 detects a position of the index image and determines whether the index image is already within the set alignment acceptable area or not. When the index image is not within the alignment acceptable area, the computer 238 controls the actuator 231 so as to enter the index image into the alignment acceptable area, detects a position of the index image again, and determines whether the index image is within the set alignment acceptable area or not.

When the index image is within the alignment acceptable area, eye refractive power as inherent information of the eye E is measured by a known method. In this embodiment, an arbitrary number of measurements can be set by a switch for setting the number of measurements, provided in the operation device 239. Here, if the number of measurements is set to be, for example, N, after a first measurement is completed, the computer 238 again detects a position of the index image, determines whether the index image is within the set alignment acceptable area or not. When the index image is not within the alignment acceptable area, the computer 238 controls the actuator 231. When the index image is within the alignment acceptable area, the next measurement for eye refractive power is performed.

Then, when the Nth measurement is completed, measurement operation is stopped and the actuator 231 is controlled with a predetermined amount so as to measure the other eye not yet be measured. When an anterior eye part image of the other eye not to be measured is picked by the observing optical system, a center position of the pupil of the other eye not yet measured is detected to start a measurement operation. After this, the above operation is performed until the number of measurements reaches N times. When the Nth measurement is completed, a measurement result is displayed on the display unit 241 and outputted to a printer (not shown), and then the entire measurement operation is completed.

As described above, it is said that the center of a pupil of the human eye does not necessarily coincide with a vertex of a cornea thereof, but rather these become eccentric in many cases. Thus, with respect to the eye E in which eccentricity of the vertex of the cornea to the center of the pupil is large, when the alignment between a cornea vertex as a standard and a measurement optical axis of the apparatus is performed, there is a fear that a light flux necessary to measure information inherent to the eye is shaded by the pupil.

However, in this embodiment, with respect to such an eye, a center position of the pupil is detected and the actuator 231 is controlled to approximately align a measurement optical axis with the center position of the pupil. Simultaneously, a position of the index image located in the vicinity of the cornea vertex is detected, an alignment acceptable area is set with a position of the index image as the center, and the actuator 231 is controlled so as to enter the index image into this area. As a result, the measurement optical axis is aligned with the center of the pupil, and the light flux necessary for the measurement is not shaded by the pupil.

Also, in the case where the position of the index image is detected, a memory area which is scanned becomes small and detection can be performed at a short time than in the case where the center position of the pupil is detected. Thus, an alignment time can be shortened and a load to a person to be examined can be decreased.

In this embodiment, although the measurement light source 217 is separated from the index light source 223, by removing the mirror 212, the projection lens 221, the cornea index 222 and the index light source 223, a light flux from the measurement light source 217 may be used also as an index light flux. Thus, the apparatus can be simplified and miniaturized.

Further, in this embodiment, a light source is disposed on an optical axis. However, a plurality of light sources are disposed symmetrically outside an optical axis, a plurality of cornea reflected light source images (index images) due to the plurality of light sources are detected, and the alignment is performed by controlling the actuator 231 such that these images are symmetrical with the measurement optical axis, so that the same effect is obtained.

Fifth Embodiment

Figure 20:
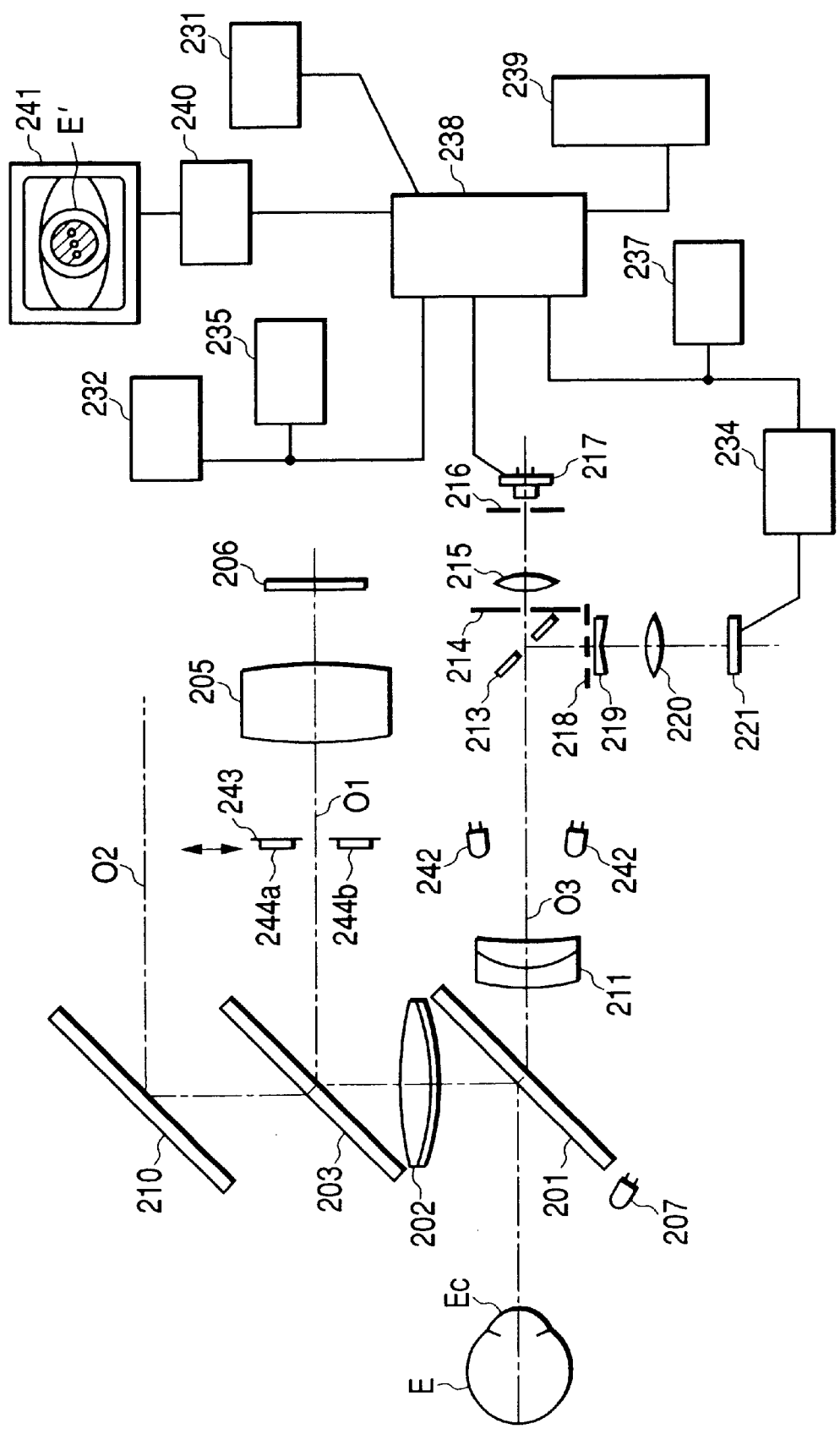
FIG. 20 shows an optical structure according to a fifth embodiment.

FIG. 20 shows a structure of an ophthalmologic apparatus according to a fifth embodiment of the present invention. In FIG. 20, the same references as those in FIG. 18 represent the same members. In the fourth embodiment, an optical system for projecting a cornea index for alignment onto the cornea Ec of the eye E from an approximate optical axis is constructed by the objective lens 211, the beam splitter 212, the projection lens 221, the cornea index 222 and the index light source 223. In contrast, in the fifth embodiment, index light source 242 such as an LED are disposed symmetrically outside an optical axis in a back side of the objective lens 211. An optical system for projecting a cornea index is constructed by the index light source 242 and the objective lens 211.

Figure 21:
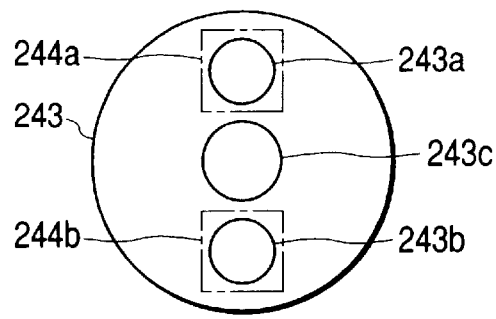
FIG. 21 is a front view of a stop plate.

Also, an aperture (stop) plate 243 is disposed on an optical axis 01. As shown in FIG. 21, the stop plate 243 has two apertures 243a and 243b provided symmetrically outside the optical axis, and an aperture 243c provided on the optical axis. Deflection prisms 244a and 244b are located close to the apertures 243a and 243b, respectively. The index light sources 241 and 242 emit light having a wavelength which is different from a wavelength of light emitted from the illuminating light source 207 and which is equal to a wavelength of light emitted from the measurement light source 217. The apertures 243a and 243b are formed to transmit only light having a wavelength emitted from the measurement light source 217 and the index light sources 241 and 242. The deflection prism 244a is constructed to deflect a light flux to a back side of a plane of the Drawing sheet, and the deflection prism 244b is constructed to deflect a light flux to a front side of the plane of the Drawing sheet.

Figure 22:
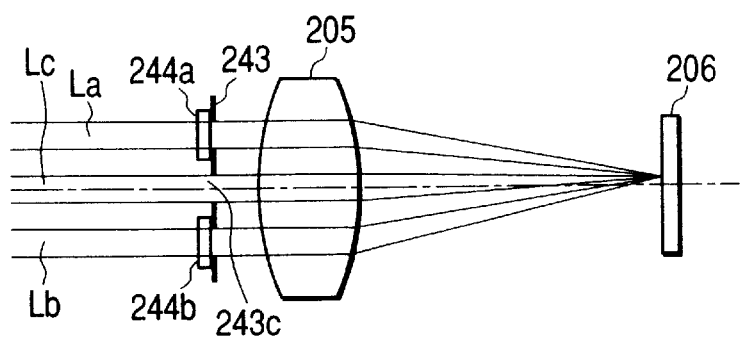
FIG. 22 is an explanatory diagram of a cornea reflected index light flux in the case where a distance is suitable.
Figure 23:
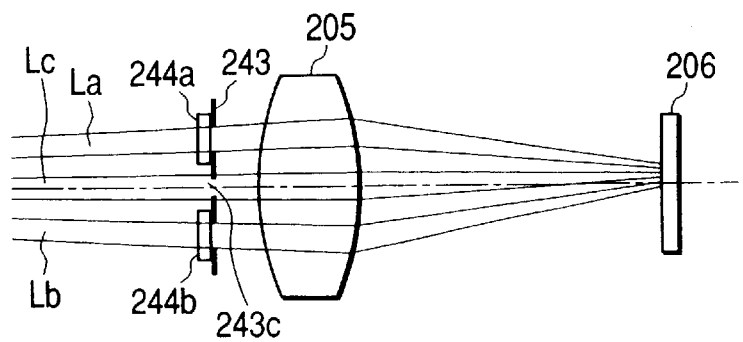
FIG. 23 is an explanatory diagram of a cornea reflected index light flux in the case where the distance is too short.
Figure 24:
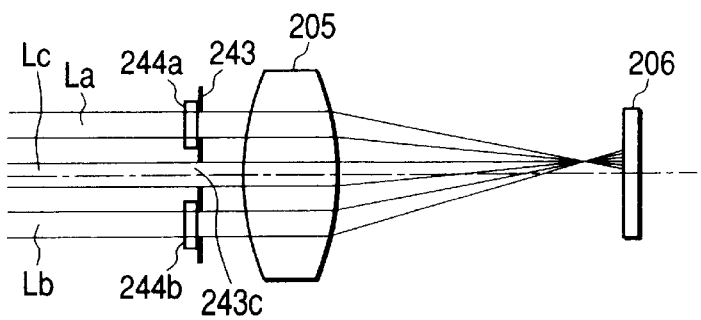
FIG. 24 is an explanatory diagram of a cornea reflected index light flux in the case where the distance is too long.

Here, the alignment between the eye E and an optical system of the apparatus will be explained. FIGS. 22 to 24 are views to explain the state where a light flux emitted from the index light source 242 is projected to the cornea Ec by the objective lens 211, a light flux reflected from the cornea Ec is passed through the dichroic mirror 201, the lens 202 and the dichroic mirror 203, divided and deflected by the deflection prism 244a and 244b and the stop plate 243, and led to the image pickup device 206 by the imaging lens 205. FIG. 22 represents the case where a distance between the eye E and the apparatus is suitable, FIG. 23 represents the case where the apparatus is too near to the eye, and FIG. 24 represents the case where the apparatus is too far from the eye.

A light flux Lc is limited by the aperture 243c. A light flux La is limited by the aperture 243a and deflected by the deflection prism 244a to a back side of the paper of the Drawing sheet. A light flux Lb is limited by the aperture 243b and deflected by the deflection prism 244b to a front side of the paper of the Drawing sheet.

Figure 25:
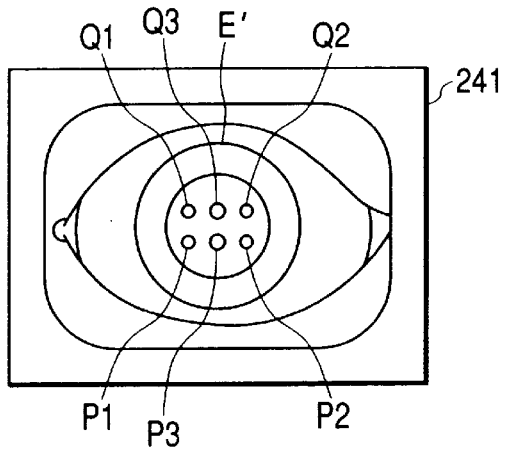
FIG. 25 is an explanatory diagram of an anterior eye part image displayed on a display unit in the case where a distance is suitable.
Figure 26:
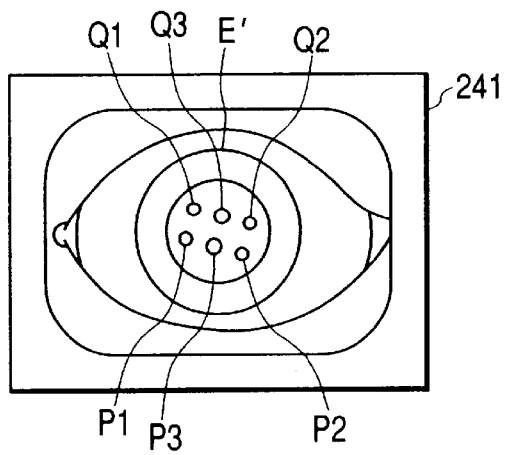
FIG. 26 is an explanatory diagram of an anterior eye part image displayed on the display unit in the case where the distance is too short.
Figure 27:
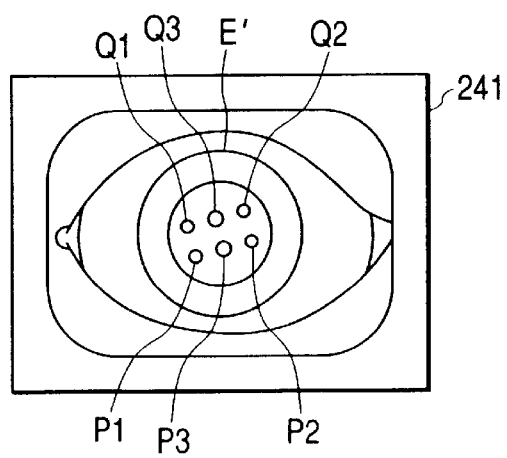
FIG. 27 is an explanatory diagram of an anterior eye part image displayed on the display unit in the case where the distance is too long.

FIGS. 25 to 27 show an anterior eye part image E' displayed on the display unit 241 after the alignment with a center position of the pupil is performed. References P1, P2 and P3 represent images obtained by dividing a light flux from the index light source 241 by the apertures 243a, 243b and 243c of the stop plate 243. References Q1, Q2 and Q3 represent images obtained by dividing a light flux from the index light source 242 by the apertures 243a, 243b and 243c of the stop plate 243. FIG. 25 represents the case where a distance between the eye E and the apparatus is suitable, FIG. 26 represents the case where the apparatus is too near to the eye, and FIG. 27 represents the case where the apparatus is too far from the eye.

As described above, in the fifth embodiment, positions of the index light source images P1, P2, P3, Q1, Q2 and Q3 reflected from the cornea Ec are detected, and then the actuator 231 is controlled, so that the alignment between the eye E and the apparatus can be performed with a suitable distance. Also, since the index light sources 241 and 242 are disposed symmetric to a measurement optical axis, by detecting positions of the index light source images P3 and Q3 reflected from the cornea Ec and calculating a middle point of these positions, a position of a cornea vertex can be obtained.

Then, similar to the fourth embodiment, an alignment acceptable area is set around the calculated position of the cornea vertex, whether the position of the cornea vertex is within the set acceptable area or not is determined. When the position of the cornea vertex is not within the area, the actuator 231 is controlled, the position of the cornea vertex is calculated again, and whether the position of the cornea vertex is within the set acceptable area or not is determined. When the position of the cornea vertex is within the acceptable area, eye refractive power is measured.

Also, the index light sources are disposed symmetric to a measurement optical axis, and the prisms which divide a reflected light flux by the cornea from the light sources into a plurality of light fluxes and deflect the divided light fluxes are provided. As a result, a cornea vertex of the eye can be detected, a distance between the eye and the apparatus can be made suitable, and a cornea vertex can be calculated based on the plurality of cornea index images obtained.

In the ophthalmologic examination method mentioned above, with respect to the eye with which eccentricity of the vertex of the cornea to the center of the pupil is large, a center position of the pupil is detected and the actuator is controlled to approximately align a measurement optical axis with the center position of the pupil. Simultaneously, a position of the index image located in the vicinity of the cornea vertex is detected, an alignment acceptable area is set with a position of the index image as the center, and the actuator is controlled so as to enter the index image into this acceptable area. As a result, the measurement optical axis is aligned with the center of the pupil, the light flux necessary for measurement is not shaded by the pupil.

Also, in the case where the position of the index image is detected, a memory area to be scanned becomes small and detection can be performed at a short time than in the case where the center position of the pupil is detected. Thus, an alignment time can be shortened and a load to a person to be examined can be decreased.

Further, after the alignment to the center of the pupile and the center of the pupil is detected, the index light source is turned on. As the result, the detection of the pupil is not influenced by a reflected light due to a cornea index light in the case where the center position of the pupil is detected.

By commonly using the measurement light source and the index light source, the apparatus can be simplified and miniaturized.

The plurality of light sources are disposed outside a measurement optical axis optically symmetrical with respect to the light axis, a plurality of cornea reflected light source images (index images) due to the plurality of light sources are detected, and the alignment is performed by controlling the actuator such that these images are symmetrical with the measurement optical axis. As a result, a detection area of the index image can be enlarged.

By providing the prisms which divide a reflected light flux by the cornea from the index light sources into a plurality of light fluxes and deflect the divided light fluxes, a cornea vertex of the eye can be detected and a distance between the eye and the apparatus can be made suitable.

What is claimed is:

1. An ophthalmologic apparatus comprising:
a measuring system for measuring inherent information of an eye;
a detecting system for detecting a standard position of the eye;
an actuator for actuating an optical system including the measuring system and the detecting system; and
a controller for dividing a processing procedure of alignment between the standard position of the eye and the measuring system in accordance with each of a plurality of areas, and changing a control method for at least one of the measuring system and the actuator in accordance with an area in which the standard position is located.

2. An ophthalmologic apparatus according to claim 1, further comprising an light source for measurement and index projection commonly, and an optical system for performing both pickup of an index image and observation of the eye.

3. An ophthalmologic apparatus according to claim 1, wherein the controller controls to perform measurement by the measuring system plural times.

4. An ophthalmologic apparatus according to claim 1, wherein the plurality of areas have a first area which is a measurement acceptable area of a relative position between the standard position and the measuring system, a second area which is within the first area and is smaller than the first area, and a third area which is outside the first and second areas, and
the controller has a first step of determining that the standard position is within which of the first, second and third areas, a second step of controlling the actuator so as to enter the standard position into the second area, and a third step of allowing measurement, and performs the second and third steps when the standard position is within the first area in the first step, performs the third step when the standard position is within the second area in the first step, and performs the second step when the standard position is within the third area in the first step.

5. An ophthalmologic apparatus according to claim 1, wherein the detecting system has a system for projecting an index light flux for alignment and dividing the index light flux reflected from the eye into a plurality of light flux.

6. An ophthalmologic apparatus according to claim 1, further comprising a display for displaying the eye with the plurality of areas.

7. An ophthalmologic apparatus according to claim 1, wherein the controller controls to start measurement automatically when the standard position of the eye is within the processing procedure.

8. An ophthalmologic apparatus comprising:
a measuring system for measuring inherent information of an eye;
an index system for projecting an index light flux onto a cornea of the eye;
an image pickup device for picking an anterior eye part of the eye together with an index image of an index light flux reflected from the cornea;
a display for displaying an anterior eye part image picked by the image pickup device together with the index image;
an operation device for allowing an operator to operate; and
a controller for detecting a position of the index image in accordance with operation by the operation device, and performing control to display an alignment mark representing a position of the index image around the index image on the display.

9. An ophthalmologic apparatus according to claim 8, further comprising an indicator for indicating to the operator whether the index image is within an area represented by the alignment mark or not.

10. An ophthalmologic apparatus according to claim 8, wherein the controller determines whether the index image is within an area represented by the alignment mark or not, and controls to automatically repeat measurement executed by the measuring system predetermined times when the index image is within the area.

11. An ophthalmologic apparatus according to claim 8 wherein the controller determines whether the index image is within an area represented by the alignment mark or not, and controls to automatically stop measurement executed by the measuring system when the index image is not within the area.

12. An ophthalmologic apparatus according to claim 11, wherein after the measurement is stopped, the controller determines whether the index image is within the area represented by the alignment mark or not, and controls to automatically restart the measurement when the index image is within the area.

13. An ophthalmologic apparatus comprising:
a measuring system for measuring inherent information of an eye;
an index system for projecting an index light flux onto a cornea of the eye;
a first detecting system for detecting a position of a pupil of the eye;
a second detecting system for detecting a position of an index image in accordance with a reflected light flux from the cornea by a light flux projected from the index system;
an actuator for actuating a unit including the measuring system, the index system, the first detecting system and the second detecting system; and
a controller for performing a first step of controlling the actuator so as to align an optical axis of the measuring system with the position of the center of the pupil detected by the first detecting system, a second step of determining an area of a predetermined range including the position of the index image as a center detected by the second detecting system, approximately simultaneous with completion of the first step, and a third step of controlling the actuator so as to enter the index image into the area.

14. An ophthalmologic apparatus according to claim 13, further comprising an image pickup device for picking an anterior eye part of the eye and a display for displaying the anterior eye part image, wherein the area determined in the second step is displayed on the display.

15. An ophthalmologic apparatus according to claim 13, further comprising a light source commonly used for the index system and the measuring system.

16. An ophthalmologic apparatus according to claim 13, further comprising an image pickup device commonly used for the first and second detecting systems.

17. An ophthalmologic apparatus according to claim 13, wherein the controller controls so as to project the index light flux into the eye by the index system after the first step is performed.

18. An ophthalmologic apparatus according to claim 13, wherein the second detecting system includes an aperture having a plurality of holes in a plane approximately vertical to the optical axis.

19. An ophthalmologic apparatus comprising:
   a measuring system for measuring inherent information of an eye;
   an index system for projecting an index light flux onto a cornea of the eye;
   a first detecting system for detecting a position of a pupil of the eye;
   a second detecting system for detecting a position of an index image in accordance with a reflected light flux from the cornea by a light flux projected from the index system;
   an actuator for actuating a unit including the measuring system, the index system, the first detecting system and the second detecting system; and
   a controller for performing a first step of controlling the actuator so as to align an optical axis of the measuring system with the position of the center of the pupil detected by the first detecting system, a second step of, approximately simultaneous with completion of the first step, obtaining a position of a vertex of the cornea from the position of the index image detected by the second detecting system and determining an area of a predetermined range including the position of the vertex of the cornea as a center, and a third step of controlling the actuator so as to enter the vertex of the cornea into the area.

20. An ophthalmologic apparatus according to claim 19, further comprising an image pickup device for picking an anterior eye part image of the eye and a display for displaying the anterior eye part image, wherein the area determined in the second step is displayed on the display.

21. An ophthalmologic apparatus according to claim 19, further comprising a light source commonly used for the index system and the measuring system.

22. An ophthalmologic apparatus according to claim 19, further comprising an image pickup device commonly used for the first and second detecting systems.

23. An ophthalmologic apparatus according to claim 19, wherein the controller controls so as to project the index light flux into the eye by the index system after the first step is performed.

24. An ophthalmologic apparatus according to claim 19, wherein the second detecting system includes an aperture having a plurality of holes in a plane approximately vertical to the optical axis.

* * * * *

UNITED STATES PATENT AND TRADEMARK OFFICE
CERTIFICATE OF CORRECTION

PATENT NO.    : 6,494,577 B2
DATED         : December 17, 2002
INVENTOR(S)   : Tomoyuki Iwanaga It is certified that error appears in the above-identified patent and that said Letters Patent is hereby corrected as shown below:

Column 1,
Line 18, "an" (2$^{nd}$ occurrence) should read -- a --.

Column 2,
Line 29, "an" should read -- a --.

Column 8,
Line 56, "is" should read -- are --.

Column 13,
Line 7, "An" should read -- A --.

Column 20,
Line 13, "be" should read -- to be --.

Column 22,
Line 46, "pupile" should read -- pupil --.

Column 23,
Line 17, "an" should read -- a --.

Signed and Sealed this

Nineteenth Day of August, 2003

JAMES E. ROGAN
*Director of the United States Patent and Trademark Office*